United States Patent
Haick et al.

(10) Patent No.: US 9,696,311 B2
(45) Date of Patent: Jul. 4, 2017

(54) DETECTION OF CANCER THROUGH BREATH COMPRISING A SENSOR ARRAY COMPRISING CAPPED CONDUCTIVE NANOPARTICLES

(75) Inventors: Hossam Haick, Haifa (IL); Peng Gang, Hunan (CN); Orna Adams, Kiryat Tivon (IL)

(73) Assignee: Technion Research and Development Foundation Ltd., Haifa (IL)

( * ) Notice: Subject to any disclaimer, the term of this patent is extended or adjusted under 35 U.S.C. 154(b) by 272 days.

(21) Appl. No.: 13/143,227

(22) PCT Filed: Jan. 10, 2010

(86) PCT No.: PCT/IL2010/000021
§ 371 (c)(1),
(2), (4) Date: Jul. 5, 2011

(87) PCT Pub. No.: WO2010/079490
PCT Pub. Date: Jul. 15, 2010

(65) Prior Publication Data
US 2011/0269632 A1    Nov. 3, 2011

Related U.S. Application Data

(60) Provisional application No. 61/143,413, filed on Jan. 9, 2009.

(51) Int. Cl.
G01N 33/574 (2006.01)
G01N 33/497 (2006.01)
(Continued)

(52) U.S. Cl.
CPC ........ *G01N 33/57423* (2013.01); *B82Y 15/00* (2013.01); *G01N 33/574* (2013.01);
(Continued)

(58) Field of Classification Search
None
See application file for complete search history.

(56) References Cited

U.S. PATENT DOCUMENTS 5,571,401 A    11/1996 Lewis
5,698,089 A    12/1997 Lewis
(Continued)

FOREIGN PATENT DOCUMENTS

CN    101135689 A    3/2008
EP    1215485    6/2002
(Continued)

OTHER PUBLICATIONS

Sun et al., Science, 287, (2000), pp. 1989-1991.*
(Continued)

*Primary Examiner* — Kaijiang Zhang
(74) *Attorney, Agent, or Firm* — Winston & Strawn LLP

(57) ABSTRACT

Sensor array for detecting biomarkers for cancer in breath samples. The sensor array is based on 2D films or 3D assemblies of conductive nanoparticles capped with an organic coating wherein the nanoparticles are characterized by a narrow size distribution. Methods of use of the sensor array for discriminating between patterns of volatile organic compounds from healthy individuals and patients with various types of cancer are disclosed.

22 Claims, 24 Drawing Sheets

(51) Int. Cl.
 B82Y 15/00 (2011.01)
 G01N 33/00 (2006.01)
(52) U.S. Cl.
 CPC ..... *G01N 33/0034* (2013.01); *G01N 33/0047* (2013.01); *G01N 2033/4975* (2013.01)

(56) References Cited

U.S. PATENT DOCUMENTS

| | | | |
|---|---|---|---|
| 6,010,616 | A | 1/2000 | Lewis |
| 6,537,498 | B1 | 3/2003 | Lewis |
| 6,746,960 | B2 | 6/2004 | Goodman |
| 6,773,926 | B1 | 8/2004 | Freund |
| 6,890,715 | B1 | 5/2005 | Lewis |
| 7,052,854 | B2 | 5/2006 | Melker |
| 2005/0079551 | A1* | 4/2005 | Mizuno et al. ............ 435/7.1 |
| 2005/0287552 | A1* | 12/2005 | Lin et al. ............... 435/6 |
| 2007/0114138 | A1 | 5/2007 | Krasteva |
| 2009/0049890 | A1* | 2/2009 | Zhong et al. ........ G01N 33/497 73/23.3 |

FOREIGN PATENT DOCUMENTS

| | | |
|---|---|---|
| FR | 2783051 | 3/2000 |
| WO | 99/27357 | 6/1999 |
| WO | 00/00808 | 1/2000 |
| WO | 00/14520 | 3/2000 |
| WO | 2009/066293 | 5/2009 |

OTHER PUBLICATIONS

Shi et al., Appl. Phys. Lett., 78, 1243 (2001).*
Han et al, Sensors and Actuators B, 106, 2005, p. 431-441.*
Toerker et al., "Annealed decanethiol monolayers on Au(111)—intermediate phases between structures with high and low molecular surface density," Surface Science 2000, 445:100-108.*
Boiselle, Phillip M. et al., (2000) Lung cancer detection in the 21st Century: Potential contributions and challenges of emerging technologies. AJR 175(5):1215-1221.
Brust, Mathias et al., (1994) Synthesis of Thiol-derivatised Gold Nanoparticles in a Two-phase Liquid-Liquid System. J Chem Soc Chem Commun 7:801-802.
Chen, Xing et al., (2005) A study of an electronic nose for detection of lung cancer based on a virtual SAW gas sensors array and imaging recognition method. Meas. Sci. Technol. 16(8):1535-1546.
Chen, Xing et al., (2007) A study of the volatile organic compounds exhaled by lung cancer cells in vitro for breath diagnosis. Cancer 110(4):835-844.
Coelho, Leiliane et al., (2007) Breath air analysis and its use as a biomarker in biological monitoring of occupational and environmental exposure to chemical agents. J Chromatography B 853(1-2):1-9.
Di Natale, Corrado et al., (2003) Lung cancer identification by the analysis of breath by means of an array of non-selective gas sensors. Biosensors and Bioelectronics 18(10):1209-1218.
Dovgolevsky, Ekaterina et al., (2010) Monolayer-Capped Cubic Platinum Nanoparticles for Sensing Nonpolar Analytes in Highly Humid Atmospheres. J. Phys. Chem. C 114(33):14042-14049.
Ebeler, Susan E. et al., (1997) Quantitative analysis by gas chromatography of volatile carbonyl compounds in expired air from mice and human. J Chromatog B 702(1-2):211-215.
Evans, Stephen D. et al., (2000) Vapour sensing using hybrid organic-inorganic nanostructured materials. J Mater Chem 10:183-188.
Hostetler, Michael J. et al., (1998) Alkanethiolate Gold Cluster Molecules with Core Diameters from 1.5 to 5.2 nm: Core and Monolayer Properties as a Function of Core Size. Langmuir 14(1):17-30.
Jemal, Ahmedin et al., (2008) Cancer Statistics, 2008. CA Cancer J Clin 58(2):71-96.

Ibanez, Francisco J. and Zamborini, Francis P. (2008) Chemiresistive Sensing of Volatile Organic Compounds with Films of Surfactant-Stabilized Gold and Gold_Silver Alloy Nanoparticles. ACS Nano 2(8):1543-1552.
Joseph, Yvonne et al., (2008) Gold nanoparticlelorganic networks as chemiresistor coatings: The effect of film morphology on vapor sensitivity. J Phys Chem C 112(32):12507-12514.
Li, Bo et al., (2007) Inkjet printed chemical sensor array based on polythiophene conductive polymers. Sensors and Actuators B 123(2):651-660.
Lonergan, Mark C. et al., (1996) Array-based vapor sensing using chemically sensitive, carbon black-polymer resistors. Chem Mater 8(9):2298-2312.
Machado, Roberto F. et al., (2005) Detection of lung cancer by sensor array analyses of exhaled breath. Am J Respir Crit Care Med 171(11):1286-1291.
Mazzone, Peter J. et al., (2007) Diagnosis of lung cancer by the analysis of exhaled breath with a colorimetric sensor array. Thorax 62(7):565-568.
Mazzone, Peter J. et al., (2008) Analysis of volatile organic compounds in the exhaled breath for the diagnosis of lung cancer. J Thorac Oncol 3(7):774-780.
O'Neill, H. J. et al., (1988) A computerized classification technique for screening for the presence of breath biomarkers in lung cancer. Clin Chem 34(8):1613-1617.
Ouyang, Gangfeng and Pawliszyn, Janusz (2006) SPME in environmental analysis. Anal Bioanal Chem 386 (4):1059-1073.
Pang, Pengfei et al., (2005) Humidity effect on the monolayer-protected gold nanoparticles coated chemiresistor sensor for VOCs analysis. Talanta 65(5):1343-1348.
Peng, Gang et al., (2008) Detecting simulated patterns of lung cancer biomarkers by random network of single-walled carbon nanotubes coated with nonpolymeric organic materials. Nano Lett 8(11):3631-3635.
Peng, Gang et al., (2009) Diagnosing lung cancer in exhaled breath using gold nanoparticles. Nat Nanotechnol 4 (10):669-673.
Phillips, Michael et al., (1999) Volatile organic compounds in breath as markers of lung cancer: a cross-sectional study. Lancet 353(9168):1930-1933.
Phillips, Michael et al., (2007) Prediction of lung cancer using volatile biomarkers in breath. Cancer Biomark 3 (2):95-109.
Raman, Baranidharan (2008) Bioinspired Methodology for Artificial Olfaction. Anal. Chem. 80(22):8364-8371.
Silkoff, P. E. et al., (2005) ATS/ERS Recommendations for Standardized Procedures for the Online and Offline Measurement of Exhaled Lower Respiratory Nitric Oxide and Nasal Nitric Oxide, 2005. Am J Respir Crit Care Med 171 (8):912-930.
Smith, David et al., (2003) Quantification of acetaldehyde released by lung cancer cells in vitro using selected ion flow tube mass spectrometry. Rapid Commun. Mass Spectrom. 17(8): 845-850.
Steinecker, William H. et al., (2007) Model of Vapor-Induced Resistivity Changes in Gold-Thiolate Monolayer-Protected Nanoparticle Sensor Films. Anal Chem 79(13):4977-4986 and supporting information.
Wehinger, Andreas et al., (2007) Lung cancer detection by proton transfer reaction mass-spectrometric analysis of human breath gas. International Journal of Mass Spectrometry 265(1):49-59.
Wohltjen, Hank and Snow, Arthur W. (1998) Colloidal Metal-Insulator-Metal Ensemble Chemiresistor Sensor. Anal Chem 70(14):2856-2859.
Zhao, Xiao-Mei et al., (1997) Soft lithographic methods for nanofabrication. J. Mater. Chem. 7(7):1069-1074.
Zhang, H.-L. et al., (2002) Vapour sensing using surface functionalized gold nanoparticles. Nanotechnology 13 (3):439-444.
The World Health Report 2004. Annex Table 2 Deaths by cause, sex and mortality stratum in WHO regions, estimates for 2002. The World Health Organization. available at http://www.who.int/whr/2004/en/.
ISR of PCT/IL2010/000021 mailed Jun. 10, 2010 (5 pages).
Kuzmych et al. (2007) Carbon Nanotube sensors for exhaled breatch components, Nanotechnology 18 375502 (7 pages).
Meyer et al. Medical Process—Uremia, Review Article, N Engl J Med 2007; 357: 1316-25.

(56) References Cited

OTHER PUBLICATIONS

Paska et al. Enhanced Sensing of Nonpolar Volatile Organic Compounds by Silicon Nanowire Field Effect Transistors ACS NANO—vol. 5, No. 7, 5620-26 (Jun. 7, 2011).
Mazzone, Progress in the development of a diagnostic test for lung cancer through the analysis of breath volatiles, J. Breath Res 2 (2008) 037014 (7 pages).
Peng et al. Detection of nonpolar molecules by means of carrier scattering in random networks of carbon nanotubes: toward diagnosis of diseases via breath samples, Nano letters 2009 vol. 9, No. 4 1362-1368.
Geng Song et al., (2008) The quantitative detection of the trace amount of the volatile organic compound in the breath of the lung cancer patient in early stage. Journal of Anhui pharmaceutical university 43(3): 323-325. Translated abstract on p. 325.
Guo et al., (2008) An Exploration into Modes of Response of a Chemiresistor Sensor Array of Gold-Nanoparticles to Volatile Organic Gases. Journal of Jining Medical College 31(3): 193-197. Translated.

\* cited by examiner

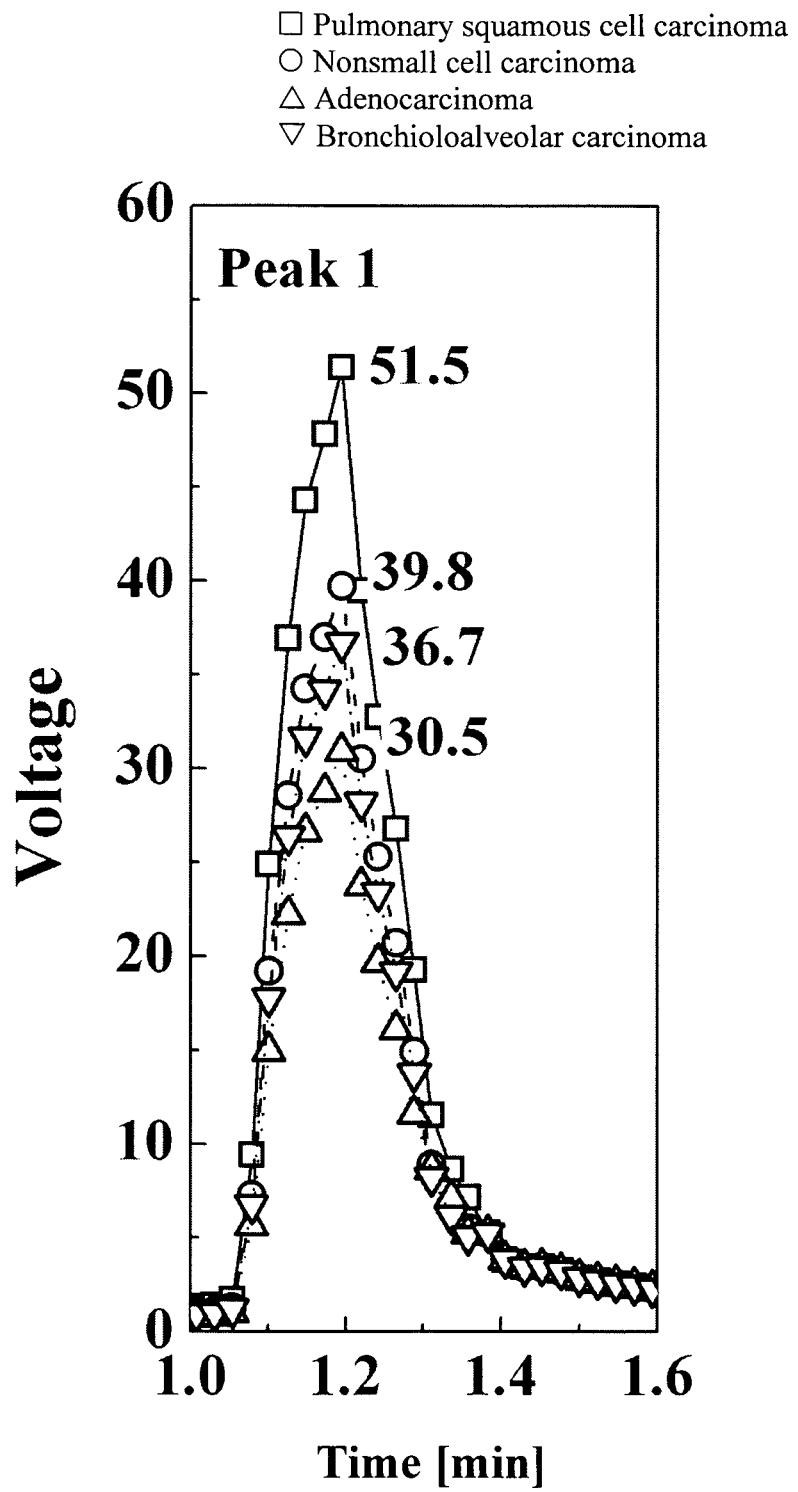

DETECTION OF CANCER THROUGH BREATH COMPRISING A SENSOR ARRAY COMPRISING CAPPED CONDUCTIVE NANOPARTICLES

REFERENCE TO CO-PENDING APPLICATIONS

Priority is claimed as a U.S. national entry under 35 U.S.C. 371 of PCT/IL2010/000021, filed on Jan. 10, 2010; which claims priority to U.S. provisional patent application Ser. No. 61/143,413, filed on Jan. 9, 2009.

FIELD OF THE INVENTION

The present invention relates to a breath analyzer comprising an array of sensors of conductive nanoparticles capped with an organic coating for detecting cancer.

BACKGROUND OF THE INVENTION

Breath analysis has long been recognized as a reliable technique for diagnosing certain medical conditions through the detection of volatile organic compounds (VOCs) in exhaled breath. The diagnosis is usually performed by collecting breath samples to a container followed by subsequent measurements of specific VOCs using mass spectrometry.

The composition of VOCs in exhaled breath is dependent upon cellular metabolic processes and it includes, inter alia, saturated and unsaturated hydrocarbons, oxygen containing compounds, sulfur containing compounds, and nitrogen containing compounds. In healthy individuals, the composition provides a distinct chemical signature with relatively narrow variability between samples from a single individual and samples from different individuals.

In exhaled breath of patients with cancer, elevated levels of certain VOCs including, volatile $C_4$-$C_{20}$ alkane compounds, specific monomethylated alkanes as well as benzene derivatives were found (Phillips et al., *Cancer Biomark.*, 3(2), 2007, 95). Hence, the composition of VOCs in exhaled breath of patients with cancer differs from that of healthy individuals, and can therefore be used to diagnose cancer. An additional advantage for diagnosing cancer through breath is the non-invasiveness of the technique which holds the potential for large-scale screening.

Gas-sensing devices for the detection of VOCs in breath samples of cancer patients have recently been applied. Such devices perform odor detection through the use of an array of cross-reactive sensors in conjunction with pattern recognition methods. In contrast to the "lock-and-key" model, each sensor in the electronic nose device is widely responsive to a variety of odorants. In this architecture, each analyte produces a distinct fingerprint from an array of broadly cross-reactive sensors. This configuration may be used to considerably widen the variety of compounds to which a given matrix is sensitive, to increase the degree of component identification and, in specific cases, to perform an analysis of individual components in complex multicomponent (bio) chemical media. Pattern recognition algorithms can then be applied to the entire set of signals, obtained simultaneously from all the sensors in the array, in order to glean information on the identity, and concentration of the vapor exposed to the sensor array.

The hitherto used gas-sensing devices comprise a variety of sensor arrays including conductive polymers, nonconductive polymer/carbon black composites, metal oxide semiconductors, fluorescent dye/polymer systems, quartz microbalance sensors coated with metallo-porphyrins, polymer coated surface acoustic wave devices, and chemoresponsive dyes (Mazzone, *J. Thoracic Onc.*, 3(7), 2008, 774). Di Natale et al. (*Biosen. Bioelec.*, 18, 2003, 1209) disclosed the use of eight quartz microbalance gas sensors coated with different metalloporphyrins for analyzing the composition of breath of patients with lung cancer. Chen et al. (*Meas. Sci. Technol.*, 16, 2005, 1535) used a pair of surface acoustic wave (SAW) sensors, one coated with a thin polyisobutylene (PIB) film, for detecting VOCs as markers for lung cancer. Machado et al. (*Am. J. Respir. Crit. Care Med.*, 171, 2005, 1286) demonstrated the use of a gaseous chemical sensing device comprising a carbon polymer sensor system with 32 separate sensors for diagnosing lung cancer. Mazzone et al. (*Torax*, 62, 2007, 565) disclosed a colorimetric sensor array composed of chemically sensitive compounds impregnated on a disposable cartilage for analyzing breath samples of individuals with lung cancer and other lung diseases. The results presented in these disclosures have yet to provide the accuracy or consistency required for clinical use.

Sensors based on films composed of nanoparticles capped with an organic coating ("NPCOCs") were applied as chemiresistors, quartz crystal microbalance, electrochemical sensors and the like. The advantages of NPCOCs for sensing applications stem from enhanced sensing signals which can be easily manipulated through varying the nanoparticles and/or aggregate size, inter-particle distance, composition, and periodicity. Enhanced selectivity can further be achieved through modifying the binding characteristics of the capping film as well as linker molecules. The morphology and thickness of NPCOC networks were shown to induce a dramatic influence on sensor response, wherein changes in permittivity induced a decrease in resistance of NPCOC thinner films (Joseph et al., *J. Phys. Chem. C*, 112, 2008, 12507). The three dimensional assembly of NPCOC structures provides additional framework for signal amplifications. Other advantages stem from the coupling of nanostructures to solid-state substrates which enable easy array integration, rapid responses, and low power-driven portable apparatuses.

Some examples for the use of NPCOCs for sensing applications are disclosed in U.S. Pat. Nos. 5,571,401, 5,698,089, 6,010,616, 6,537,498, 6,746,960, 6,773,926; Patent Application Nos. WO 00/00808, FR 2,783,051 US 2007/0114138; and in Wohltjen et al. (*Anal. Chem.*, 70, 1998, 2856), and Evans et al. (*J. Mater. Chem.*, 8, 2000, 183).

International patent application publication number WO 99/27357 discloses an article of manufacture suitable for use in determining whether or in what amount a chemical species is present in a target environment, which article comprises a multiplicity of particles in close-packed orientation, said particles having a core of conductive metal or conductive metal alloy, in each said particle such core being of 0.8 to 40.0 nm in maximum dimension, and on said core a ligand shell of thickness from 0.4 to 4.0 nm, which is capable of interacting with said species such that a property of said multiplicity of particles is altered.

U.S. Pat. No. 7,052,854 discloses systems and methods for ex-vivo diagnostic analysis using nanostructure-based assemblies comprising a nanoparticle, a means for detecting a target analyte/biomarker, and a surrogate marker. The sensor technology is based on the detection of the surrogate marker which indicates the presence of the target analyte/biomarker in a sample of a bodily fluid.

EP 1,215,485 discloses chemical sensors comprising a nanoparticle film formed on a substrate, the nanoparticle film comprising a nanoparticle network interlinked through linker molecules having at least two linker units. The linker units are capable of binding to the surface of the nanoparticles and at least one selectivity-enhancing unit having a binding site for reversibly binding an analyte molecule. A change of a physical property of the nanoparticle film is detected through a detection means.

WO 2009/066293 to one of the inventors of the present invention discloses a sensing apparatus for detecting volatile and non-volatile compounds, the apparatus comprises sensors of cubic nanoparticles capped with an organic coating. Further disclosed are methods of use thereof in detecting certain biomarkers for diagnosing various diseases and disorders including cancer.

There is an unmet need for a fast responsive sensor array based on a variety of sensors which provide improved sensitivity as well as selectivity for specific VOCs indicative of cancer.

SUMMARY OF THE INVENTION

The present invention provides a sensor array for detecting volatile organic compounds (VOCs) indicative of various types of cancer. The sensor array comprises conductive nanoparticles capped with an organic coating wherein the nanoparticles are characterized by a narrow particle size distribution and wherein the thickness of the organic coating is tailored to provide increased sensitivity. The present invention further provides a system comprising the sensor array in conjunction with a learning and pattern recognition analyzer, and methods of use thereof in diagnosing various types of cancer through breath.

The invention is based in part on the unexpected finding that a sensor array comprising conductive nanoparticles capped with an organic coating wherein the nanoparticles are characterized by a narrow particle size distribution provides enhanced sensitivities for detecting VOCs. It was not previously realized that the use of nanoparticles having well defined and narrow particle size distribution enhances the efficacy of electron transfer to provide improved signal to noise ratios. Increased sensitivity is further induced by fine-tuning of the thickness of the organic coating.

According to one aspect, the present invention provides a sensor array for detecting VOCs indicative of cancer comprising conductive nanoparticles capped with an organic coating, the nanoparticles having a narrow particle size distribution with a mean particle size of about 5 nm and particle size in the range of about 1-10 nm, and wherein the thickness of the organic coating is in the range of about 0.2-4 nm.

According to another aspect, the present invention provides a system for detecting a pattern of VOCs indicative of cancer comprising a sensor array comprising conductive nanoparticles capped with an organic coating, the nanoparticles having a narrow particle size distribution with a mean particle size of about 5 nm and particle size in the range of about 1-10 nm, and wherein the thickness of the organic coating is in the range of about 0.2-4 nm, and further comprising a learning and pattern recognition analyzer wherein the learning and pattern recognition analyzer receives sensor signal outputs and compares them to stored data.

In one embodiment the nanoparticles have particle size in the range of about 2-8 nm. In another embodiment, the nanoparticles have particle size in the range of about 3-6 nm.

In a particular embodiment, the thickness of the organic coating is in the range of about 0.6-2 nm.

In some embodiments, the conductive nanoparticles are selected from metals and metal alloys. According to certain embodiments, the conductive nanoparticles comprise metals and metal alloys selected from the group consisting of Au, Ag, Ni, Co, Pt, Pd, Cu, Al, Au/Ag, Au/Cu, Au/Ag/Cu, Au/Pt, Au/Pd, Au/Ag/Cu/Pd, Pt—Rh, Ni—Co, and Pt—Ni—Fe. Each possibility represents a separate embodiment of the invention.

In various embodiments, the coating of the conductive nanoparticles comprises a monolayer or multilayers of organic compounds, wherein the organic compounds can be small molecules, monomers, oligomers or polymers, preferably short polymeric chains. In particular embodiments, the organic compounds are selected from the group consisting of alkylthiols, arylthiols, alkylarylthiols, alkylthiolates, ω-functionalized alkylthiolates, arenethiolates, (γ-mercaptopropyl)tri-methyloxysilane, dialkyl sulfides, diaryl sulfides, alkylaryl sulfides, dialkyl disulfides, diaryl disulfides, alkylaryl disulfides, alkyl sulfites, aryl sulfites, alkylaryl sulfites, alkyl sulfates, aryl sulfates, alkylaryl sulfates, xanthates, oligonucleotides, polynucleotides, dithiocarbamate, alkyl amines, aryl amines, diaryl amines, dialkyl amines, alkylaryl amines, arene amines, alkyl phosphines, aryl phosphines, dialkyl phosphines, diaryl phosphines, alkylaryl phosphines, phosphine oxides, alkyl carboxylates, aryl carboxylates, dialkyl carboxylates, diaryl carboxylates, alkylaryl carboxylates, cyanates, isocyanates, peptides, proteins, enzymes, polysaccharides, phospholipids, and combinations and derivatives thereof. Each possibility represents a separate embodiment of the invention.

In a particular embodiment, the organic coating comprises alkylthiols with $C_3$-$C_{24}$ chains.

In other embodiments, the sensors of conductive nanoparticles capped with an organic coating are in a configuration selected from the group consisting of 1D wires, 2D films, and 3D assemblies. Each possibility represents a separate embodiment of the invention.

In yet other embodiments, the system of the present invention further comprises an apparatus for collecting breath samples. In specific embodiments, the system of the present invention comprises an apparatus for collecting alveolar breath. In another embodiment, the system of the present invention further comprises at least one of a breath concentrator and a dehumidifying unit.

In particular embodiments, the system of the present invention further comprises at least one of a chemiresistor, chemicapacitor, quartz crystal microbalance (QCM), bulk acoustic wave (BAW) and surface acoustic wave (SAW) resonator, electrochemical cell, surface plasmon resonance (SPR), and optical spectroscope. Each possibility represents a separate embodiment of the invention.

In various embodiments, the learning and pattern recognition analyzer utilizes various algorithms including, but not limited to, artificial neural networks, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical algorithms including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor. Each possibility represents a separate embodiment of the invention.

According to yet another aspect, the present invention provides a method of diagnosing cancer in a subject, the method comprising the steps of: (a) providing a system comprising a sensor array comprising conductive nanoparticles capped with an organic coating, the nanoparticles having a narrow particle size distribution with a mean particle size of about 5 nm and particle size distribution in the range of about 1-10 nm, and wherein the thickness of the organic coating is in the range of about 0.2-4 nm, and further comprising a learning and pattern recognition analyzer wherein the learning and pattern recognition analyzer receives sensor signal outputs and compares them to stored data, (b) exposing the sensor array to exhaled breath sample, and (c) using learning and pattern recognition algorithms to determine the presence of a pattern of volatile organic compounds indicative of cancer in the sample.

In certain embodiments, the method for detecting VOCs indicative of cancer in a breath sample further comprises the step of increasing breath analyte concentrations using at least one of a breath concentrator and a dehumidifying unit.

In specific embodiments, the method of diagnosing cancer through the detection of VOCs indicative of cancer comprises measuring a change in any one or more of conductivity, resistance, impedance, capacitance, inductance, or optical properties of the sensors upon exposure to VOCs to be detected. Each possibility represents a separate embodiment of the invention.

In a particular embodiment, the method according to the principles of the present invention comprises the use of spectroscopic ellipsometry for detecting VOCs indicative of cancer.

In various embodiments, the method of diagnosing cancer in a subject comprises the detection of volatile organic compounds selected from the group consisting of 4-methyloctane, 2-ethyl-1-hexanol, 2-ethyl-4-methyl-1-pentanol, 2,3,4-trimethyl-pentane, 2,3-dimethyl-hexane, trimethylsilyl fluoride, dimethyl-silanediol, 3-ethyl-3-methyl-2-pentanone, 2-methyl-4,6-octadiyn-3-one, 2-propyl-1-pentanol, decane, trimethyl benzene, ethyl benzene, heptanol, isoprene, hexane, undecane and 6,10-dimethyl-5,9-dodecadien-2-one. Each possibility represents a separate embodiment of the invention.

Encompassed within the scope of the present invention is the diagnosis of various cancers including, but not limited to, lung, brain, ovarian, colon, prostate, kidney, bladder, breast, oral, and skin cancers. Each possibility represents a separate embodiment of the invention.

According to particular embodiments, the present invention provides a method of diagnosing cancer selected from the group consisting of lung cancer, breast cancer, colon cancer, head and neck cancer, and prostate cancer. Each possibility represents a separate embodiment of the invention.

In certain embodiments, the method disclosed herein further provides the discrimination between breath samples of patients having different types of cancer. In particular embodiments, the present invention provides the discrimination between breath samples of patients having different stages of a single type of cancer selected from lung cancer, breast cancer, colon cancer, head and neck cancer, and prostate cancer. Each possibility represents a separate embodiment of the invention. In exemplary embodiments, the present invention provides the discrimination between patients having lung cancer selected from the group consisting of pulmonary squamous cell carcinoma, adenocarcinoma, bronchioloalveolar carcinoma, and nonsmall cell carcinoma. Each possibility represents a separate embodiment of the invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
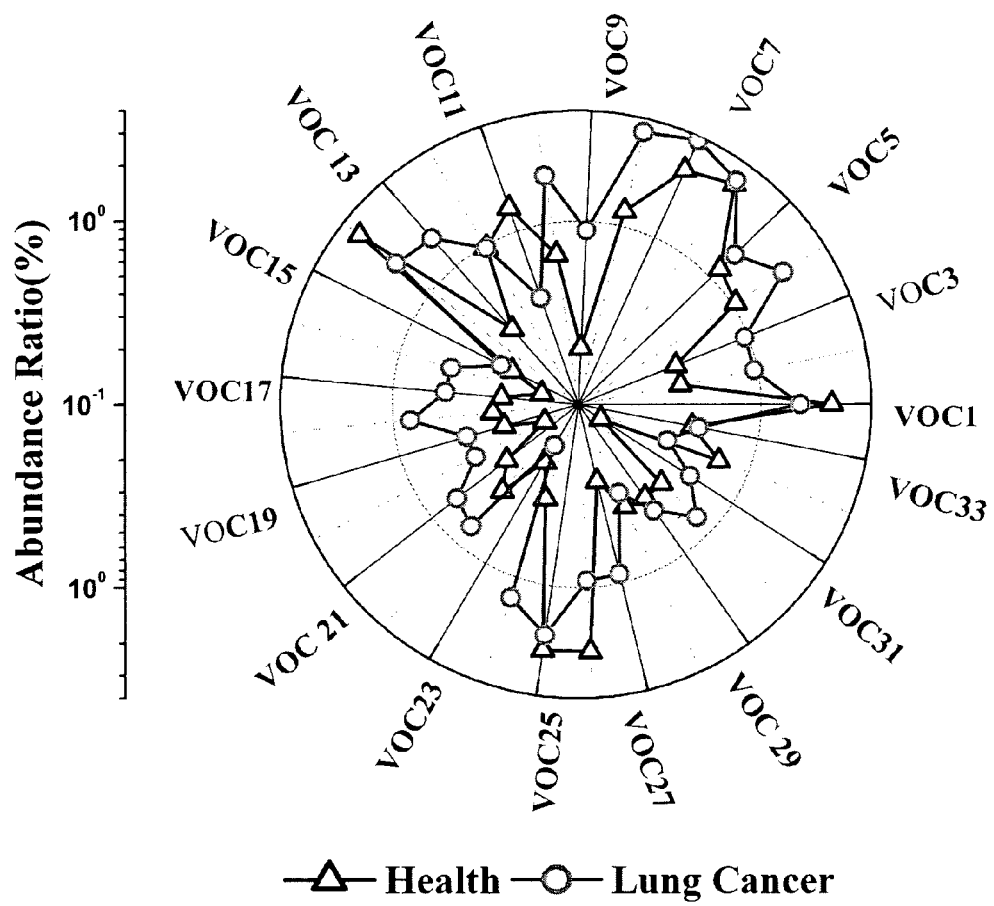
FIG. 1. Average abundance of 33 VOCs which were found in breath samples of healthy individuals (triangles) and patients having lung cancer (circles) as measured by GC-MS.

The present invention provides a sensor array comprising conductive nanoparticles capped with an organic coating wherein the nanoparticles are characterized by a narrow particle size distribution. The thickness of the organic coating is tailored to provide enhanced sensitivities for particular volatile organic compounds indicative of various types of cancer. The present invention further provides a system comprising the sensor array in conjunction with a learning and pattern recognition analyzer which utilized various algorithms to enable the identification of particular volatiles from a mixture of volatiles. Methods of use thereof for diagnostic, prognostic and monitoring purposes are further disclosed.

The sensor array, according to the principles of the present invention is designed for detecting volatile organic compounds indicative of cancer. Upon adsorption of an analyte, the film/assembly of conductive nanoparticles capped with an organic coating (NPCOCs) can either swell, or aggregate. In thin films of NPCOCs a relative change in the permittivity constant of the film upon analyte adsorption may be generated. The response introduced upon analyte exposure is determined by the nature of the interaction between analyte (host) species and the molecular coating of the nanoparticles. It is now disclosed for the first time that using nanoparticles with narrow size distribution capped with an organic coating of varying thickness enables the detection of cancer biomarkers in breath with very high accuracy. Within the scope of the present invention is the detection of VOCs with sensitivity of less than one part per million (ppm), and more preferably less than 100 parts per billion (ppb).

Without being bound by any theory or mechanism of action, it is contemplated that sensors composed of nanoparticles having a narrow size distribution are more sensitive to analyte adsorption. This might be attributed to the close packing of the nanoparticles which renders them susceptible to very minor structural changes which occur upon analyte adsorption. These structural changes of the nanoparticle assemblies affect the electronic properties to induce electronic responses. It is contemplated that a sensing response can be induced by very small amounts of analyte molecules according to the principles of the present invention. Further sensitivity can be achieved through varying the thickness of the organic coating.

Nanoparticles utilized in the present invention have a particle size ranging from about 1 nanometer (nm) to about 10 nanometers, preferably from about 2 nm to about 8 nm. In particular embodiments, the mean particle size of the nanoparticles is about 5 nm with narrow particle size distribution wherein the particle size ranges from about 3 nm to about 6 nm.

The size distribution of the nanoparticles, according to the principles of the present invention, is narrow. The term "narrow particle size distribution" as used herein refers to a distribution wherein more than 90% of the particles have a particle size in the range of 0.2-2 times the mean (or average) particle size. Preferably, more than 95% of the particles have a particle size within this range. Even more preferably more than 99% of the particles have a particle size within this range. Thus, for a mean particle size of 5 nm, a narrow size distribution refers to a distribution wherein more than 90%, 95% or 99% of the particles have a particle size in the range of 1-10 nm.

Nanoparticle size distribution is usually defined in terms of the mean particle size and the width of the distribution. The width of the distribution curve at one half of the maximum value is termed full width at half maximum (FWHM). The relationship between the FWHM and mean particle size is used as a measure of broadness or narrowness of the distribution. For example, a distribution having a FWHM value that is larger than the mean particle size is considered relatively broad. As discussed above, the nanoparticles used in the present invention have a narrow particle size distribution. An alternative definition of narrow particle size distribution for the nanoparticles used in the present invention is a distribution in which the FWHM of the distribution curve is equal to the difference between the mean particle size plus 40% of the mean and the mean particle size minus 40% of the mean. In particular, the FWHM of the distribution curve is equal to two times 40% of the mean, i.e. 80% of the mean. Thus, a narrow particle size distribution refers to a distribution wherein the FWHM is less than or equal to 80% of the mean particle size. In some embodiments, the FWHM is less than or equal to 60% of the mean particle size. In other particular embodiments, the FWHM is less than or equal to 40% of the mean particle size. The nanoparticles are essentially spherical or spheroidal in shape.

According to the principles of the present invention, the mean particle size as used herein refers to the average particle diameter which can be determined, for example, using Transmission Electron Microscopy (TEM). The mean particle size can further be determined using other techniques known to those of skill in the art including, but not limited to, sedimentation flow fractionation, photon correlation spectroscopy, light scattering, electron scattering, disk centrifugation, and the like.

Another important feature of the present invention is the thickness of the organic coating which influences the sensitivity to adsorption of different biomarker analytes. In specific embodiments, the organic coating has thickness in the range of about 0.2 nm to about 4 nm. In some embodiments, the sensor array comprises sensors having nanoparticles of a single species capped with various organic compounds wherein the thickness of the organic coating ranges from about 0.6 nm to about 2 nm. In other embodiments, the sensor array comprises sensors having nanoparticles of a single species capped with various organic compounds wherein the thickness of the organic coating ranges from about 0.2 nm to about 2 nm for some nanoparticles and from about 2 nm to about 4 nm for other nanoparticles. In alternative embodiments, the sensor array comprises sensors having nanoparticles of various species.

The present invention further provides a system for detecting at least one pattern of VOCs indicative of cancer comprising a sensor array comprising conductive nanoparticles capped with an organic coating wherein the nanoparticles are characterized by a narrow size distribution, wherein the particle size of the nanoparticles ranges from about 1 nm to about 10 nm with a mean particle size of about 5 nm and wherein the thickness of the organic coating ranges from about 0.2 nm to about 4 nm, and further comprising a learning and pattern recognition analyzer wherein the learning and pattern recognition analyzer receives sensor signal outputs and compares them to stored data.

According to certain embodiments, the conductive nanoparticles comprise metals and/or metal alloys. Suitable non-limiting examples are metals of Au, Ag, Ni, Co, Pt, Pd, Cu, Al; and metal alloys of Au/Ag, Au/Cu, Au/Ag/Cu, Au/Pt, Au/Pd, Au/Ag/Cu/Pd, Pt—Rh, Ni—Co, and Pt—Ni—Fe. In an exemplary embodiment, the conductive nanoparticles are selected from the group consisting of Au, Ag, and Pt. Each possibility represents a separate embodiment of the invention.

The coating of the conductive nanoparticles comprises a monolayer or multilayers of organic compounds, wherein the organic compounds can be small molecules, monomers, oligomers or polymers (preferably short polymeric chains). In particular embodiments, the organic compounds are selected from the group consisting of alkylthiols, e.g., alkylthiols with $C_3$-$C_{24}$ chains, arylthiols, alkylarylthiols, alkylthiolates, ω-functionalized alkylthiolates, arenethiolates, (γ-mercaptopropyl)tri-methyloxysilane, dialkyl sulfides, diaryl sulfides, alkylaryl sulfides, dialkyl disulfides, diaryl disulfides, alkylaryl disulfides, alkyl sulfites, aryl sulfites, alkylaryl sulfites, alkyl sulfates, aryl sulfates, alkylaryl sulfates, xanthates, oligonucleotides, polynucleotides, dithiocarbamate, alkyl amines, aryl amines, diaryl amines, dialkyl amines, alkylaryl amines, arene amines, alkyl phosphines, dialkyl phosphines, aryl phosphines, diaryl phosphines, alkylaryl phosphines, dialkyl phosphines, diaryl phosphines, alkylaryl phosphines, phosphine oxides, alkyl carboxylates, aryl carboxylates, dialkyl carboxylates, diaryl carboxylates, alkylaryl carboxylates, dialkyl carboxylates, diaryl carboxylates, alkylaryl carboxylates, cyanates, isocyanates, peptides, proteins, enzymes, polysaccharides, phospholipids, and combinations and derivatives thereof. Each possibility represents a separate embodiment of the invention.

Other organic compounds suitable as capping agents include, but are not limited to, alkenyl thiols, alkynyl thiols, cycloalkyl thiols, heterocyclyl thiols, heteroaryl thiols, alkenyl thiolates, alkynyl thiolates, cycloalkyl thiolates, heterocyclyl thiolates, heteroaryl thiolates, alkenyl sulfides, alkynyl sulfides, cycloalkyl sulfides, heterocyclyl sulfides, heteroaryl sulfides, alkenyl disulfides, alkynyl disulfides, cycloalkyl disulfides, heterocyclyl disulfides, heteroaryl disulfides, alkenyl sulfites, alkynyl sulfites, cycloalkyl sulfites, heterocyclyl sulfites, heteroaryl sulfites, alkenyl sulfates, alkynyl sulfates, cycloalkyl sulfates, heterocyclyl sulfates, heteroaryl sulfates, alkenyl amines, alkynyl amines, cycloalkyl amines, heterocyclyl amines, heteroaryl amines, alkenyl carboxylates, alkynyl carboxylates, cycloalkyl carboxylates, heterocyclyl carboxylates, and heteroaryl carboxylates. Each possibility represents a separate embodiment of the invention.

An "alkyl" group refers to a saturated aliphatic hydrocarbon, including straight-chain, branched-chain and cyclic alkyl groups. In one embodiment, the alkyl group has 1-12 carbons designated here as $C_1$-$C_{12}$-alkyl. In another embodiment, the alkyl group has 2-6 carbons designated here as $C_2$-$C_6$-alkyl. In another embodiment, the alkyl group has 2-4 carbons designated here as $C_2$-$C_4$-alkyl. In an exemplary embodiment, the alkyl group has 3-24 carbons designated here as $C_3$-$C_{24}$ alkyl. The alkyl group may be unsubstituted or substituted by one or more groups selected from halogen, haloalkyl, acyl, amido, ester, cyano, nitro, and azido. Each possibility represents a separate embodiment of the invention.

A "cycloalkyl" group refers to a non-aromatic mono- or multicyclic ring system. In one embodiment, the cycloalkyl group has 3-10 carbon atoms. In another embodiment, the cycloalkyl group has 5-10 carbon atoms. Exemplary monocyclic cycloalkyl groups include cyclopentyl, cyclohexyl, cycloheptyl and the like. An alkylcycloalkyl is an alkyl group as defined herein bonded to a cycloalkyl group as defined herein. The cycloalkyl group can be unsubstituted or substituted with any one or more of the substituents defined above for alkyl.

An "alkenyl" group refers to an aliphatic hydrocarbon group containing at least one carbon-carbon double bond including straight-chain, branched-chain and cyclic alkenyl groups. In one embodiment, the alkenyl group has 2-8 carbon atoms (a $C_{2-8}$ alkenyl). In another embodiment, the alkenyl group has 2-4 carbon atoms in the chain (a $C_{2-4}$ alkenyl). Exemplary alkenyl groups include, but are not limited to, ethenyl, propenyl, n-butenyl, i-butenyl, 3-methylbut-2-enyl, n-pentenyl, heptenyl, octenyl, cyclohexylbutenyl and decenyl. An alkylalkenyl is an alkyl group as defined herein bonded to an alkenyl group as defined herein. The alkenyl group can be unsubstituted or substituted through available carbon atoms with one or more groups defined hereinabove for alkyl.

An "alkynyl" group refers to an aliphatic hydrocarbon group containing at least one carbon-carbon triple bond including straight-chain and branched-chain. In one embodiment, the alkynyl group has 2-8 carbon atoms in the chain (a $C_{2-8}$ alkynyl). In another embodiment, the alkynyl group has 2-4 carbon atoms in the chain (a $C_{2-4}$ alkynyl). Exemplary alkynyl groups include, but are not limited to, ethynyl, propynyl, n-butynyl, 2-butynyl, 3-methylbutynyl, n-pentynyl, heptynyl, octynyl and decynyl. An alkylalkynyl is an alkyl group as defined herein bonded to an alkynyl group as defined herein. The alkynyl group can be unsubstituted or substituted through available carbon atoms with one or more groups defined hereinabove for alkyl.

An "aryl" group refers to an aromatic monocyclic or multicyclic ring system. In one embodiment, the aryl group has 6-10 carbon atoms. The aryl is optionally substituted with at least one "ring system substituents" and combinations thereof as defined herein. Exemplary aryl groups include, but are not limited to, phenyl or naphthyl. An alkylaryl is an alkyl group as defined herein bonded to an aryl group as defined herein. The aryl group can be unsubstituted or substituted through available carbon atoms with one or more groups defined hereinabove for alkyl.

A "heteroaryl" group refers to a heteroaromatic system containing at least one heteroatom ring wherein the atom is selected from nitrogen, sulfur and oxygen. The heteroaryl contains 5 or more ring atoms. The heteroaryl group can be monocyclic, bicyclic, tricyclic and the like. Also included in this definition are the benzoheterocyclic rings. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

A "heterocyclic ring" or "heterocyclyl" group refers to a five-membered to eight-membered rings that have 1 to 4 heteroatoms, such as oxygen, sulfur and/or in particular nitrogen. These five-membered to eight-membered rings can be saturated, fully unsaturated or partially unsaturated, with fully saturated rings being preferred. Exemplary heterocyclic rings include, but are not limited to, piperidinyl, pyrrolidinyl pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. An alkylheterocyclyl is an alkyl group as defined herein bonded to a heterocyclyl group as defined herein. The heterocyclyl group can be unsubstituted or substituted through available atoms with one or more groups defined hereinabove for alkyl.

"Ring system substituents" refer to substituents attached to aromatic or non-aromatic ring systems including, but not limited to, H, halo, haloalkyl, $(C_1-C_8)$alkyl, $(C_2-C_8)$alkenyl, $(C_2-C_8)$alkynyl, $(C_6-C_{10})$aryl, acyl, amido, ester, cyano, nitro, azido, and the like.

A "halogen" or "halo" group as used herein alone or as part of another group refers to chlorine, bromine, fluorine, and iodine. The term "haloalkyl" refers to an alkyl group having some or all of the hydrogens independently replaced by a halogen group including, but not limited to, trichloromethyl, tribromomethyl, trifluoromethyl, triiodomethyl, difluoromethyl, chlorodifluoromethyl, pentafluoroethyl, 1,1-difluoroethyl bromomethyl, chloromethyl, fluoromethyl, iodomethyl, and the like.

An "acyl" group as used herein encompasses groups such as, but not limited to, formyl, acetyl, propionyl, butyryl, pentanoyl, pivaloyl, hexanoyl, heptanoyl, octanoyl, nonanoyl, decanoyl, undecanoyl, dodecanoyl, benzoyl and the like. Currently preferred acyl groups are acetyl and benzoyl.

An "alkoxy" group refers to an —O-alkyl group wherein R is alkyl as defined above.

A "thio" group as used herein alone or as part of another group refers to an SH group. The terms "alkylthio", "arylthio" or "arylalkylthio" as used herein alone or as part of another group refer to any of the above alkyl, arylalkyl or aryl groups linked to a sulfur atom.

The terms "oligonucleotide" or "polynucleotide" as used herein refer to DNA or RNA of genomic or synthetic origin, which may be single- or double-stranded, and represent the sense or antisense strand.

The terms "peptide" and "protein" as used herein refer to a polymer of amino acid residues. The terms apply to amino acid polymers in which one or more amino acid residues is an artificial chemical analogue of a corresponding naturally occurring amino acid, as well as to naturally occurring amino acid polymers. Many more molecules that satisfy the definition of "organic coating" may be used in the same context.

According to the principles of the present invention the organic coating is characterized by varying thickness to provide enhanced sensitivities to specific volatile organic compounds indicative of cancer. Without being bound by any theory or mechanism of action, a thin layer of organic coating in the range of about 0.2-0.6 nm is more suitable for the detection of analytes having relatively low vapor pressure (<10 torr), which mainly adsorb on the surface of the coating to induce the sensing signal. A relatively thick layer of organic coating in the range of about 0.6-2 nm and, in other exemplary embodiments, 2-4 nm, is more suitable for the detection of analytes having relatively high vapor pressure (>10 torr). In this case, the analyte molecules penetrate more deeply to the core of the coating to induce the sensing signal.

According to certain embodiments, the sensors of the present invention are manufactured through a self-assembly process to produce films comprising NPCOCs. The term "self-assembly" as used herein refers to a process of organization of molecules without intervening from an outside source. The self-assembly process takes place in a solution/solvent or directly on the solid-state substrate. The term "film", as used herein, corresponds to a configuration of well-arranged assembly of NPCOCs, preferably in body centered cubic (BCC) or face centered cubic (FCC) configuration. The use of nanoparticles with narrow size distribution enables a more compact packing of the nanoparticles thus resulting in films that are more susceptible to minor changes in film structures upon analyte adsorption. These films are hence more sensitive than films which have a wide particle size distribution.

The synthesis of NPCOCs can be produced by methods known in the art. For instance, gold nanoparticles can be synthesized using the two-phase method (Brust et al., *J. Chem. Soc. Chem. Commun.*, 801, 1994, 2) with some modifications (Hostetler et al., *Langmuir*, 14 1998, 24). Briefly, $AuCl_4^-$ is transferred from aqueous $HAuCl_4.xH_2O$ solution to a toluene solution by the phase-transfer reagent TOAB. After isolating the organic phase, excess thiols are added to the solution. The mole ratio of thiol:$HAuCl_4.xH_2O$ can vary between 1:1 and 10:1, depending on the thiol used. This is performed in order to prepare mono-disperse solution of gold nanoparticles in average size of about 5 nm. Exemplary procedures include, but are not limited to, thiol:Au mole ratios of 10:1 and 1:1 for dodecanethiol and butanethiol-capped gold nanoparticles, respectively at an average size of 5 nm. After vigorous stirring of the solution, aqueous solution of reducing agent $NaBH_4$ in large excess is added. The reaction is constantly stirred at room temperature for at least 3 hours to produce a dark brown solution of the thiol-capped Au nanoparticles. The resulting solution is further subjected to solvent removal in a rotary evaporator followed by multiple washings using ethanol and toluene.

Gold nanoparticles capped with 2-mercaptobenzoazole can be synthesized by ligand-exchange method from pre-prepared hexanethiol-capped gold nanoparticles. In a typical reaction, excess of thiol, 2-mercaptobenzoazole, is added to a solution of hexanethiol-capped gold nanoparticles in toluene. The solution is kept under constant stirring for few days in order to allow as much ligand conversion as possible. The nanoparticles are purified from free thiol ligands by repeated extractions.

Without being bound by any theory or mechanism of action, it is contemplated that sensing occurs via aggregation or swelling of the conductive nanoparticles capped with an organic coating assemblies, through various chemical interactions. The interactions include, but are not limited to, hydrogen-bonding, π-π, host-guest, van der Waals, electrostatic, charge-transfer, antigen-antibody interactions, and combinations thereof. Changes in permittivity usually occur in thin films having regions of discontinuities in chemiresistors, chemicapacitors and electrochemical cells which are composed of 2D or 3D films of metallic nanoparticles.

Exemplary methods for obtaining well-ordered two or three dimensional assemblies of NPCOCs include, but are not limited to,
  i. Random deposition from solution of NPCOCs on solid surfaces. The deposition is performed by drop casting, spin coating, spray coating and other similar techniques.
  ii. Field-enhanced or molecular-interaction-induced deposition from solution of NPCOCs on solid surfaces.
  iii. Langmuir-Blodgett or Langmuir-Schaefer techniques. The substrate is vertically plunged through self-organized/well-ordered 2D monolayer of NPCOCs at the air-subphase interface, wherein the latter being subsequently transferred onto it. Multiple plunging of the substrate through the 2D monolayer of NPCOCs at the air-subphase interface, results in the fabrication of the 3D-ordered multilayers of NPCOCs.
  iv. Soft lithographic techniques, such as micro-contact printing (mCP), replica molding, micro-molding in capillaries (MIMIC), and micro-transfer molding (mTM). These methods are based on variations of self-assembly and replica molding of organic molecules and polymeric materials, for fabricating NPCOCs from nanometer-scale to a mesoscopic scale (Whitesides et al., *J. Mater. Chem.* 7, 1069, 1997).
  v. Various combinations of Langmuir-Blodgett or Langmuir-Schaefer methods with soft lithographic techniques can be used to produce patterned Langmuir-Blodgett films of molecularly modified NPCOCs which are transferred onto solid substrates.
  vi. Printing on solid-state or flexible substrates using an inject printer designated for printed electronics. A solution containing the NPCOCs is used as a filling material (or "ink") of the printing head according to procedures well known in the art as described in e.g. Holland et al. (*Ink Maker* 8, 83, 2005).

According to the principles of the present invention the sensor array for detecting volatiles indicative of cancer in breath samples comprises a plurality of sensors between 2 to 1000 sensors, more preferably between 2 to 500 sensors, even more preferably between 2 to 250 sensors, and most preferably between 2 to 125 sensors in an array. In an exemplary embodiment, the sensor array comprises 9 chemically sensitive sensors. In another exemplary embodiment, the sensor array comprises 14 chemically sensitive sensors.

In some embodiments, the present invention provides a system in which the sensor array of NPCOCs is used in conjunction with either one of a chemiresistor, chemicapacitor, quartz crystal microbalance, bulk acoustic wave (BAW) and surface acoustic wave (SAW) resonator, electrochemical cell, surface plasmon resonance (SPR), and optical spectroscope. Each possibility represents a separate embodiment of the invention.

Sensing responses upon exposure of the sensors to an analyte may be induced through a change in any one of the conductivity, resistance, impedance, capacitance, inductance, or optical properties of one or more of the sensors. Each possibility represents a separate embodiment of the invention.

For electronically induced sensing, electrical contacts of the films of NPCOCs which were deposited on a solid substrate (e.g. silica, silicon, quartz etc) for support and/or easy array integration, can be performed by methods well known in the art. Suitable methods for inducing electrical contacts include, but are not limited to, photolithography, e-beam lithography, Focused Ion Beam (FIB), direct evaporation/sputtering through shadow mask, soft (stamp) contact, inject printing techniques of conductive nanoparticles, and other similar techniques. Alternatively, films of nanoparticles can be deposited on ready-made contacts that were fabricated by the either one of the methods described hereinabove. The electrodes, according to the principles of the present invention, can be contacted at various geometries in manners well known to a skilled artisan. In one embodiment, electrodes are contacted with a distance of 15 μm between adjacent electrodes. In another embodiment, electrodes are contacted with a distance of 100 μm between adjacent electrodes. According to the principles of the present invention, the distance between two adjacent electrodes is in the range of 100 nm to 5000 μm.

In specific embodiments, sensing can be detected through changes in the optical properties a sensor network. In exemplary embodiments, sensing is carried out using spectroscopic ellipsometry. This technique measures the change in polarization upon reflection of polarized light from a surface. Without being bound by any theory or mechanism of action, the adsorption of analyte molecules induces changes in thickness of layers of NPCOCs networks. The change in thickness or roughness induces changes in polarization which can be recorded by the spectroscopic ellipsometry technique. The signal obtained is subsequently conveyed to a learning and pattern recognition analyzer to generate a result. In this manner no electrical contacts are required. The aggregation and/or swelling of NPCOCs upon analyte absorption render this technique advantageous for detecting volatiles with very high sensitivity.

Within the scope of the present invention are methods for determining at least one pattern of volatile organic compounds in a breath sample wherein the volatile organic compounds are biomarkers for cancer. The methods comprise exposing the sensor array to a sample of exhaled breath and using learning and pattern recognition algorithms in order to analyze the sensor signal and identify and possibly quantify desired compounds or patterns indicative of cancer. Thus, provided herein is a system comprising the sensor array of the present invention in conjunction with a learning and pattern recognition analyzer. The analyzer receives signal outputs or patterns from the sensor array and analyses them by various pattern recognition algorithms to produce an output signature. By sorting an unknown signature using a database of stored or known signatures, desired compounds can be identified. According to the principles of the present invention, sensing is obtained through adsorption of volatile organic compounds to provide signal changes which are then conveyed to a learning and pattern recognition analyzer to generate identification of desired compounds.

Algorithms for sample analysis include, but are not limited to, principal component analysis, Fischer linear analysis, neural network algorithms, genetic algorithms, fuzzy logic pattern recognition, and the like. After analysis is completed, the resulting information can, for example, be displayed on display, transmitted to a host computer, or stored on a storage device for subsequent retrieval.

Many of the algorithms are neural network based algorithms. A neural network has an input layer, processing layers and an output layer. The information in a neural network is distributed throughout the processing layers. The processing layers are made up of nodes that simulate the neurons by the interconnection to their nodes.

When a neural network is combined with a sensor array, the sensor data is propagated through the networks. In this mariner, a series of vector matrix multiplications are performed and unknown analytes can be readily identified and determined. The neural network is trained by correcting the false or undesired outputs from a given input. Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), Fisher linear discriminant analysis (FLDA), soft independent modeling of class analogy (SIMCA), K-nearest neighbors (KNN), neural networks, genetic algorithms, fuzzy logic, and other pattern recognition algorithms. In some embodiments, the Fisher linear discriminant analysis (FLDA) and canonical discriminant analysis (CDA) as well as combinations thereof are used to compare the output signature and the available data from the database. Each possibility represents a separate embodiment of the invention.

In other embodiments, principal component analysis is used. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

Principal component analysis compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a constant. Another relationship between matrices is that they share principal components in common, but their eigenvalues differ. The mathematical technique used in principal component analysis is called eigenanalysis. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows of this matrix.

Methods of using the sensor array for diagnosing cancer are provided herein. The methods include the detection of volatile organic compounds as cancer biomarkers from breath directly exhaled by the subject on the sensor array of the present invention. Alternatively the sensor array may be exposed to the headspace of a container wherein exhaled breath has been deposited. Other possibilities include exhaling into an inert bag and then exposing the collected breath to the sensor array of the present invention. Thus, the system of the present invention may further comprise a breath collector apparatus for collecting breath samples, particularly alveolar breath samples. Exemplary breath collector apparatus within the scope of the present invention are those approved by the American Thoracic Society/European Respiratory Society (ATS/ERS); (Silkoff et al. *Am. J. Respir. Crit. Care Med.* 171, 2005, 912). Alveolar breath is usually collected from individuals using the off-line method. However it is to be understood that breath collection directly to the device, vis-à-vis the on-line method is encompassed by the present invention. In some embodiments, no need for pre-concentrating or dehumidifying the sample prior to measurement is required. In other embodiments, where better discrimination between "control" and "cancer" breath samples is required, a breath concentrator and/or a dehumidifying unit is used.

Breath concentrators that are within the scope of the present invention include, but are not limited to, I. Solid Phase Microextraction (SPME)—The SPME technique is based on a fiber coated with a liquid (polymer), a solid (sorbent), or combination thereof. The fiber coating extracts the compounds from the sample either by absorption (where the coating is liquid) or by adsorption (where the coating is solid). The SPME fiber is then inserted directly into the sensing device for desorption and subsequent analysis (Ouyang, et al., *Anal. Bioanal. Chem.*, 386, 2006, 1059; Coelho et al., *J. Chromatography B*, 853, 2007, 1).

II. Sorbent Tubes—Sorbent tubes are typically made of glass and contain various types of solid adsorbent material (sorbents). Commonly used sorbents include activated charcoal, silica gel, and organic porous polymers such as Tenax and Amberlite XAD resins. Sorbent tubes are attached to air sampling pumps for sample collection. A pump with a calibrated flow rate in ml/min draws a predetermined volume of air through the sorbent tube. Chemicals are trapped onto the sorbent material throughout the sampling period. This technique was developed by the US National Institute for Occupational Safety and Health (NIOSH).

III. Cryogenic Concentrations—Cryogenic condensation is a process that allows recovery of volatile organic compounds (VOCs) for reuse. The condensation process requires very low temperatures so that VOCs can be condensed. Traditionally, chlorofluorocarbon (CFC) refrigerants have been used to condense the VOCs. Currently, liquid nitrogen is used in the cryogenic (less than −160° C.) condensation process.

A dehumidifier in accordance with the present invention includes the following non-limiting examples:

I. Drawing moist air over cold refrigerated coils—using this approach, the air moisture condenses into droplets as it passes through cold refrigerated coils into a container. "Dried" air then brought to its original temperature and returned to the sensing device.

II. Silica Gel—is an amorphous form of silicon dioxide, which is synthetically produced in the form of hard irregular granules or beads. A microporous structure of interlocking cavities gives a very high surface area (800 square meters per gram). This unique structure renders the silica gel as a high capacity desiccant. Water molecules adhere to the surface of the silica gel due to its low vapor pressure as compared to the surrounding air. When pressure equilibrium is reached, the adsorption ceases. Thus the higher the humidity of the surrounding air, the greater the amount of water that is adsorbed before equilibrium is reached. Silica gel is advantageous as a drying substance since the process of drying requires no chemical reaction and no by products or side effects.

III. Activated carbon—is formed by processing charcoal to an extremely porous carbon substance. Due to its high degree of microporosity the activated carbon possesses a very large surface area available for chemical reactions. Sufficient activation may be obtained solely from the high surface area, though further chemical treatment often enhances the adsorbing properties of the material.

IV. Desiccant Molecular Sieves—are synthetically produced, highly porous crystalline metal-alumino silicates. They are classified by the many internal cavities of precise diameters, namely, 3 Å, 4 Å, 5 Å, and 10 Å. Adsorption occurs only when molecules to be adsorbed have smaller diameters than the cavity openings. Molecules of high polarity are better adsorbed into the molecular sieves. Molecular sieves adsorb water molecules and other contaminants from liquids and gases down to very low levels of concentrations, often to 1 ppm.

In a particular embodiment, the method described herein is used to discriminate between different types of cancer. Gas-Chromatography linked with Mass-Spectrometry (GC-MS) studies have shown that volatile $C_4$-$C_{20}$ alkanes and certain monomethylated alkanes as well as benzene derivatives appear to be elevated in various instances of cancer. The compounds of interest are generally found in the range of 1-20 ppb in healthy human breath, but can be seen in distinctive mixture compositions at elevated levels in the range of 10-100 ppb in the breath of cancer patients. The levels of these biomarkers are elevated even at the early stages of the disease, since they reflect a change in human body chemistry. This change appears regardless of the tumor size. In addition, biomarkers of a specific disease (e.g., lung cancer) possess distinctive mixture compositions/patterns which differ from the compositions/patterns of biomarkers of other diseases. Volatile organic compounds which can be used as biomarkers for the diagnosis of cancer include, but are not limited to, 4-methyl-octane, 2-ethyl-1-hexanol, 2-ethyl-4-methyl-1-pentanol, 2,3,4-trimethyl-pentane, 2,3-dimethyl-hexane, trimethylsilyl fluoride, dimethyl-silanediol, 3-ethyl-3-methyl-2-pentanone, 2-methyl-4,6-octadiyn-3-one, 2-propyl-1-pentanol, decane, trimethyl benzene, ethyl benzene, heptanol, isoprene, hexane, undecane and 6,10-dimethyl-5,9-dodecadien-2-one. Each possibility represents a separate embodiment of the invention.

As contemplated herein, using the methods of the present invention allow the discrimination between different types of cancer. In some embodiments, the system of the present invention provides the diagnosis of a single cancer type at different stages. In other embodiments, the system of the present invention provides the discrimination between breath samples obtained from lung cancer patients at different stages (or tumor sizes) of the disease.

The term "cancer" as used herein refers to a disorder in which a population of cells has become, in varying degrees, unresponsive to the control mechanisms that normally govern proliferation and differentiation. Cancer refers to various types of malignant neoplasms and tumors, including primary tumors, and tumor metastasis. Non-limiting examples of cancers which can be detected by the sensor array and system of the present invention are brain, ovarian, colon, prostate, kidney, bladder, breast, lung, oral, and skin cancers. Specific examples of cancers are: carcinomas, sarcomas, myelomas, leukemias, lymphomas and mixed type tumors. Particular categories of tumors include lymphoproliferative disorders, breast cancer, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, as well as metastases of all the above. Particular types of tumors include hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, pulmonary squamous cell carcinoma, basal cell carcinoma, adenocarcinoma (well differentiated, moderately differentiated, poorly differentiated or undifferentiated), bronchioloalveolar carcinoma, renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

According to certain embodiments, the cancer to be diagnosed is selected from the group consisting of lung cancer, head and neck cancer, breast cancer, pancreatic cancer, lymphoma, myeloma, leukemia, kidney cancer, ovarian cancer, bone cancer, liver cancer, prostate cancer, skin cancer, colon cancer, and thyroid cancer. Each possibility represents a separate embodiment of the invention. According to exemplary embodiments, the cancer to be diagnosed is selected from breast cancer, kidney cancer, larynx cancer, vaginal tumor, stomach cancer, leukemia, including lymphoblastic leukemia, lung carcinoma, melanoma and colon cancer. Each possibility represents a separate embodiment of the invention.

Due to the miniaturized dimensions of the sensor array (in the range of 10-100 nanometers to a few micrometers), it could be installed in any electronic device including, but not limited to, a watch or cellular phone. The integration of the sensor array to a commonly used electronic device allows it to be used as a warning system for initiation of cancer.

As used herein and in the appended claims the singular forms "a", "an," and "the" include plural references unless the content clearly dictates otherwise. Thus, for example, reference to "an organic coating" includes a plurality of such organic coatings and equivalents thereof known to those skilled in the art, and so forth.

The principles of the present invention are demonstrated by means of the following non-limitative examples.

EXAMPLES

Example 1: Collection of Exhaled Breath

After deep exhaling, subjects inhaled to total lung capacity through mouthpiece that contained a cartridge on the aspiratory port, in order to remove more than 99.99% of VOC ambient contaminants from inhaled air during inspiration. Subjects then exhaled against 10-15 cm of $H_2O$ pressure to ensure closure of the vellum to exclude nasal entrainment of gas. Exhaled gas was collected through a separate exhalation port of the mouthpiece in a non-reactive Mylar gas-sampling bag (purchased from Eco Medics), which was previously cleaned with $N_2$ gas. At least five analyses were performed on the exhaled breath of each subject. A total of 90 breath samples wherein 26 were obtained from healthy individuals and 64 were obtained from lung cancer patients, was used. The patients were previously clinically diagnosed using various diagnostic methods including bronchoscope biopsy, computed tomography (CT) scan and pulmonary puncture. None of the lung cancer patients had received chemotherapy and/or other treatment before breath samples were collected.

Example 2: Analysis of Exhaled Breath by GC-MS

Exhaled breath samples from subjects with lung cancer and from healthy individuals were collected in Mylar sample bags and analyzed with gas chromatography-mass spectroscopy (GC-MS) combined with solid phase microextraction (SPME). The SPME technique is used for pre-concentrating VOCs in the breath samples. A manual SPME holder with an extraction fiber coated with: 1) Polydimethylsiloxane (PDMS), 2) Polydimethylsiloxane-Divinylbenzene (PDMS/DVB), or 3) Polydimethylsiloxane-Carboxen (PDMS/Carboxen) (purchased from Sigma-Aldrich) was inserted into the Mylar bag. Between 500 and 1,000 $cm^3$ of each breath sample was concentrated via the SPME method with extraction period of 2 hours, and delivered to GC-MS using a manual SPME holder. The extracted fiber in the manual SPME holder was inserted into GC injector which operated using the splitless model. The oven temperature profile was: 60° C., 2 min, 8° C./min to 100° C., 15° C./min to 120° C., 8° C./min to 180° C., 15° C./min to 200° C., 8° C./min to 225° C. Capillary column H5-5MS 5% Phenyl Methyl Siloxane (30 m length, 0.25 mm i.d., 0.25 µm thickness) was used. The column pressure was set to 8.22 psi, and initial flow was 1.0 mL/min. Finally, the molecular structures of the VOCs were determined via the Standart Modular Set.

GC-MS identified 33 common VOCs (Table 1) that had been either synthesized or catabolized in breath samples of healthy individuals and lung cancer patients. Of which, 11 specific VOCs (Table 2) were found only in the breath of lung cancer patients and not in the breath of healthy individuals, with at least 83% confidence. FIG. 1 shows the average abundance ratio of 33 VOCs (the corresponding name can be found in Table 1) in breath samples of healthy individuals (controls; triangles) and in breath samples of lung cancer patients (circles). The compounds detected are mostly $C_4$-$C_{20}$ straight and monomethylated alkanes in addition to certain benzene derivatives. The compounds that were observed in breath samples from healthy individuals and lung cancer patients, were present not only in different concentrations but also in distinctive mixture compositions.

FIG. 1 clearly shows that VOCs detected in breath samples of healthy individuals form a unique pattern which differs from the pattern of VOCs in breath samples of patients with lung cancer. Almost all VOCs were found to be at higher concentrations in samples of lung cancer patients with the exceptions of VOC1, VOC11, VOC14, VOC25 and VOC26.

TABLE 1

VOCs that were detected in breath samples obtained from control individuals and lung cancer patients

| Symbol | VOCs |
| --- | --- |
| VOC1 | Hydrazine-carboxamide |
| VOC2 | Hydrazine, methyl- |
| VOC3 | Ethyl alcohol |
| VOC4 | o-Xylene |
| VOC5 | Benzene, 1-methyl-4-(1-methylethyl) |
| VOC6 | Ethylbenzene |
| VOC7 | Styrene |
| VOC8 | Toluene |
| VOC9 | Dimethyl ether |
| VOC10 | Butylated Hydroxytoluene |
| VOC11 | Carbonic dihydrazide |
| VOC12 | Benzene, 1-methyl-2-(1-methylethyl)- |
| VOC13 | Benzene, 1-methyl-3-(1-methylethyl)- |
| VOC14 | 1,3,5-Cycloheptatriene |
| VOC15 | Hexane, 3-methyl |
| VOC16 | Pentane, 3-ethyl- |
| VOC17 | 1,3,5,7-Cyclooctatetraene |
| VOC18 | Bicyclo[4.2.0]octa-1,3,5-triene |
| VOC19 | Hexane, 2,3,4-trimethyl- |
| VOC20 | Phenol, 2,6-bis(1,1-dimethylethyl)-4-methyl-, methylcarbamate |
| VOC21 | Heptane, 2,4dimethyl |
| VOC22 | Undecane, 4,7-dimethyl- |
| VOC23 | 2,4,6-Tris(1,1-dimethyl-ethyl)-4-methylcyclohexa-2,5-dien-1-one |
| VOC24 | Octane,2,6,6-trimethyl |
| VOC25 | 2-Butanone |
| VOC26 | Hydrazine |
| VOC27 | 1,3-Pentadiene |
| VOC28 | Pentane, 3,3-dimethyl- |
| VOC29 | Hexane, 3,3-dimethyl- |
| VOC30 | Hexane, 2-methyl- |
| VOC31 | Hexane, 3-ethyl- |
| VOC32 | Hexane, 2,2,3-trimethyl- |
| VOC33 | Cyclopropane, ethylidene |

TABLE 2

VOCs that were detected only in breath samples of lung cancer patients

| VOCs Name | Average of abundance | Standard deviation | Percentage of patients |
| --- | --- | --- | --- |
| Octane, 4-methyl- | 0.8913% | 0.8648% | 100% |
| 1-Hexanol, 2-ethyl- | 0.3324% | 0.2378% | 91.7% |
| 1-Pentanol, 2-ethyl-4-methyl- | 0.3758% | 0.2795% | 91.7% |
| Pentane, 2,3,4-trimethyl- | 0.4054% | 0.4231% | 91.7% |
| Hexane, 2,3-dimethyl- | 1.5288% | 1.0017% | 91.7% |
| Trimethylsilyl fluoride | 1.3335% | 0.8325% | 83.3% |
| Silanediol, dimethyl- | 0.7075% | 0.5258% | 83.3% |
| 2-Pentanone, 3-ethyl-3-methyl- | 0.8339% | 0.3319% | 83.3% |
| 4,6-Octadiyn-3-one, 2-methyl- | 0.1650% | 0.0976% | 83.3% |
| 2-Propyl-1-pentanol | 0.7412% | 0.8930% | 83.3% |
| 5,9-Dodecadien-2-one, 6,10-dimethyl-, (E,E))- | 0.5493% | 0.3297% | 83.3% |

Example 3: Synthesis and Capping of Gold Nanoparticles

Gold nanoparticles having average size of about 5 nm were capped with a variety of alkanethiolates having chain lengths of $C_4$-$C_{18}$ and ω-functionalized alkanethiolate (e.g.

11-mercapto-1-unedecanol). Gold nanoparticles were synthesized using the standard two-phase method according to Brust et al. (*J. Chem. Soc., Chem. Corn.,* 801, 1994, 2), with some modifications according to Hostetler et al. (*Langmuir,* 1998, 14, 24). Briefly, $AuCl_4^-$ was first transferred from aqueous $HAuCl_4 \cdot xH_2O$ solution (25 ml, 31.5 mM) to a toluene solution by the phase-transfer reagent TOAB (80 ml, 34.3 mM). After the organic phase was isolated, excess of the thiols was then added to the solution. The mole ratio of thiol:$HAuCl_4 \cdot xH_2O$ was varied between 1:1 and 10:1 depending on kind of thiol, in order to prepare monodispersed solution of gold nanoparticles in average size of 5 nm. For example, mole ratios of thiol:Au were 10:1 and 1:1 for dodecanethiol and butanethiol-capped gold nanoparticles, respectively, at average size of 5 nm. After vigorous stirring of the solution for 10 min, aqueous solution of reducing agent $NaBH_4$ in large excess (25 mL, 0.4 M, ice-cooled) was added. The reaction was stirred at room temperature for at least 3 hours, which produced a dark brown solution of the thiol-capped gold nanoparticles. The resulting solution was subjected to solvent removal in a rotary evaporator and followed by multiple washings using ethanol and toluene.

Gold nanoparticles capped with 2-mercaptobenzoazole were synthesized by ligand-exchange method from pre-prepared hexanethiol-capped gold nanoparticles. In a typical reaction excess of incoming thiol, 2-mercaptobenzoazole (7 μg) was added to a solution of hexanethiol-capped gold nanoparticles in toluene (3 mg/ml, 5 ml). The solution was under constant stirring for few days in order to allow maximal ligand conversion. The nanoparticles were purified from free thiol ligands by repeated extractions.

The gold nanoparticles were characterized using transmission electron microscopy (TEM). Samples for TEM were prepared by dropcasting 5:1 of diluted nanoparticle solution in toluene onto 200-mesh carbon-coated copper grids. TEM images (Model CM120, Philips, The Netherlands) of the gold nanoparticles were obtained at 120 kV. Transmission electron micrographs of the gold nanoparticles confirmed the narrow size distribution of the nanoparticles with an average diameter of about 5 nm.

Example 4: Sensor Fabrication

Figure 2:
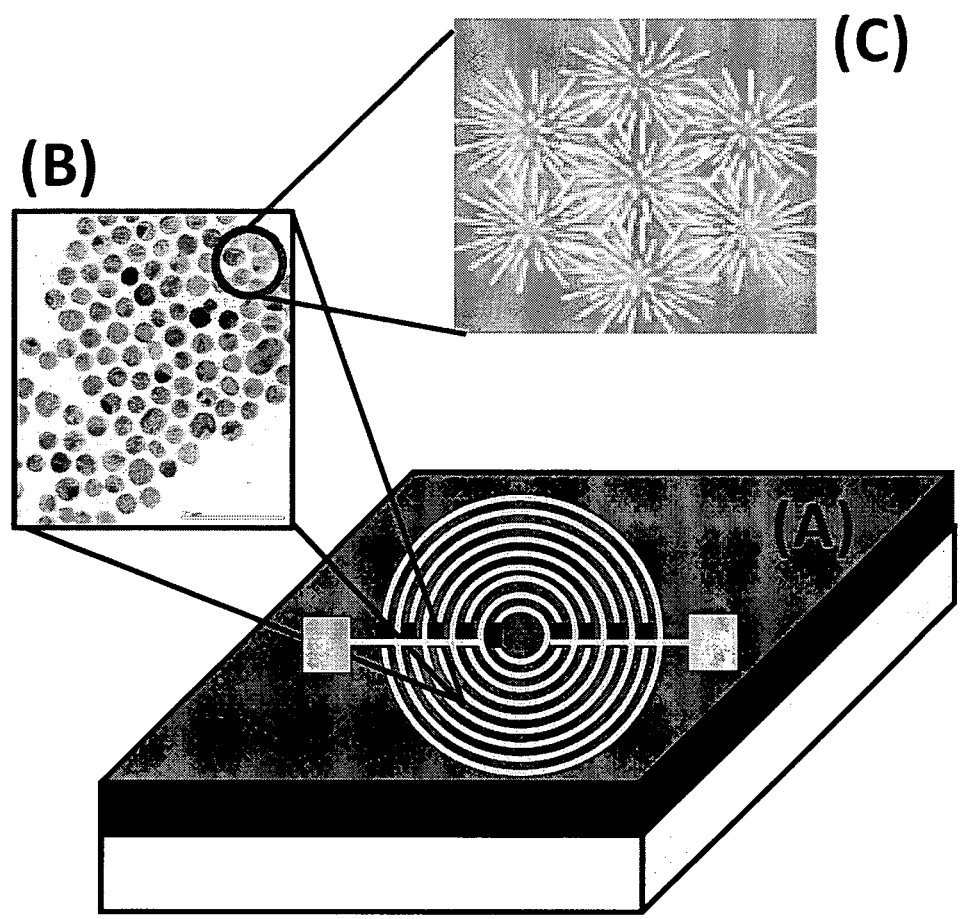
FIG. 2. (A) Schematic illustration of the sensor array of the present invention. (B) Transmission electron micrograph of gold nanoparticles which indicates that the nanoparticles have a narrow size distribution with an average diameter of about 3.5 nm. (C) Schematic representation of gold nanoparticles capped with an organic coating.

Interdigitated electrodes are firstly patterned or deposited on top of the degenerative p-doped silicon wafer having 300 nm (in thickness) $SiO_2$ film, using either lithography process or evaporation of metal through shadow mask. A schematic illustration of the device is shown in FIG. 2(A). The diameter of the spiral electrodes is approximately 3000 μm, and the gap widths of the metal electrodes are approximately 20 μm each.

In particular, functionalized gold nanoparticles (see table 3) having an average diameter of about 5 nm (FIG. 2(B) and FIG. 2(C)), were dispersed in Chloroform by sonication, followed by a drop of gold nanoparticles solution cast into the electrode. While still coated with solution, the substrate was blown with a stream of dry $N_2$. This process was repeated several times to yield the desired resistance, preferably from 20 KΩ to 5 MΩ. In other embodiments, film resistances from 5 MΩ to 80 MΩ were prepared. The device was dried for 2 hours in a fume hood at an ambient temperature, and then heated to 50° C. in a vacuum oven over night.

TABLE 3

Compounds used for coating the gold nanoparticles of the sensor array

| Sensor no. | Functional molecules |
|---|---|
| S1 | 4-methoxy-toluenethiol |
| S2 | 11-mercapto-1-undecanol |
| S3 | Decanethiol |
| S4 | 1-Butanethiol |
| S5 | 2-Ethylhexanethiol |
| S6 | 2-Mercaptobenzoazole |
| S7 | Hexanethiol |
| S8 | Tert-dodecanethiol |
| S9 | 3-Methyl-1-butanethiol |

Example 5: Response of the Sensor Array to Particular Biomarkers Indicative of Lung Cancer The developed sensors of example 4 were mounted onto a custom PTFE circuit board which had 10 separated sensor sites. The board was then mounted onto a stainless steel test chamber having a volume of less than 100 $cm^3$. An Agilent Multifunction switch 34980 controlled by USB was used to choose the active sensor and measure the corresponding resistance at a given time. The entire system was controlled by a custom Labview program.

In order to test sensor sensitivity to biomarkers indicative of lung cancer, measurements of the response to particular biomarkers was performed using a custom bubbler system according to Peng et al. (*Nano Letters,* 8(11), 2008, 5). The response was measured as $\Delta R/R_b$, wherein $R_b$ is the baseline resistance of the sensor in the absence of analyte, and $\Delta R$ is the baseline-corrected steady-state resistance change upon exposure of the sensor to an analyte.

Figure 3:
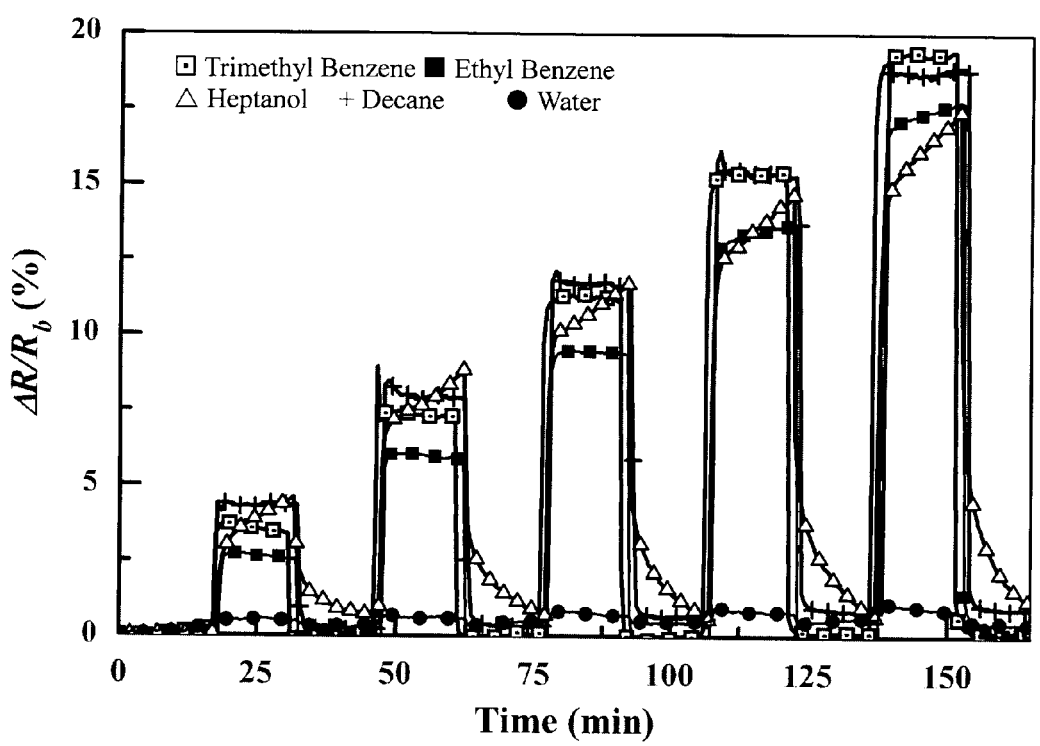
FIG. 3. Relative differential resistance response $\Delta R/R_b$ of sensor number 8 to the most common biomarkers which are present in the breath samples of lung cancer patients (i.e., decane [+], trimethyl benzene [□], ethyl benzene [■], and heptanol [△] vapors) and water vapor [●] at concentrations of 0.001-0.05 P/P°.

The response of the gold nanoparticle sensor array to the different lung cancer biomarkers at concentrations between 0.001 P/P° and 0.05 P/P° (P° is the saturated vapor pressure of the corresponding analyte at room temperature) was first examined. FIG. 3 shows the response of a gold nanoparticles sensor capped with tert-dodecanethiol (sensor number 8) to various analytes. In particular, the analytes that were used include decane, trimethyl benzene, ethyl benzene and heptanol biomarkers. As can be seen from the figure, the response of the sensor was rapid upon exposure to analyte vapor. Additionally, the response was fully reversible upon switching back to zero analyte vapor (purified, dry air). Most importantly, the sensor was responsive to a wide variety of concentrations of analyte vapors with excellent signal-to-noise ratio (typically, larger than 10).

The response of the sensor to water vapor was tested as well. This feature is significant since exhaled breath contains a high concentration of water vapors which can impede the measurements of VOCs indicative of cancer due to their relatively low concentrations in breath samples. FIG. 3 clearly shows that the responses to lung cancer biomarkers are much lager than the response to water vapors indicating the high sensitivity of the sensor to biomarkers of lung cancer even in the presence of high concentrations of water vapors.

Figure 4:
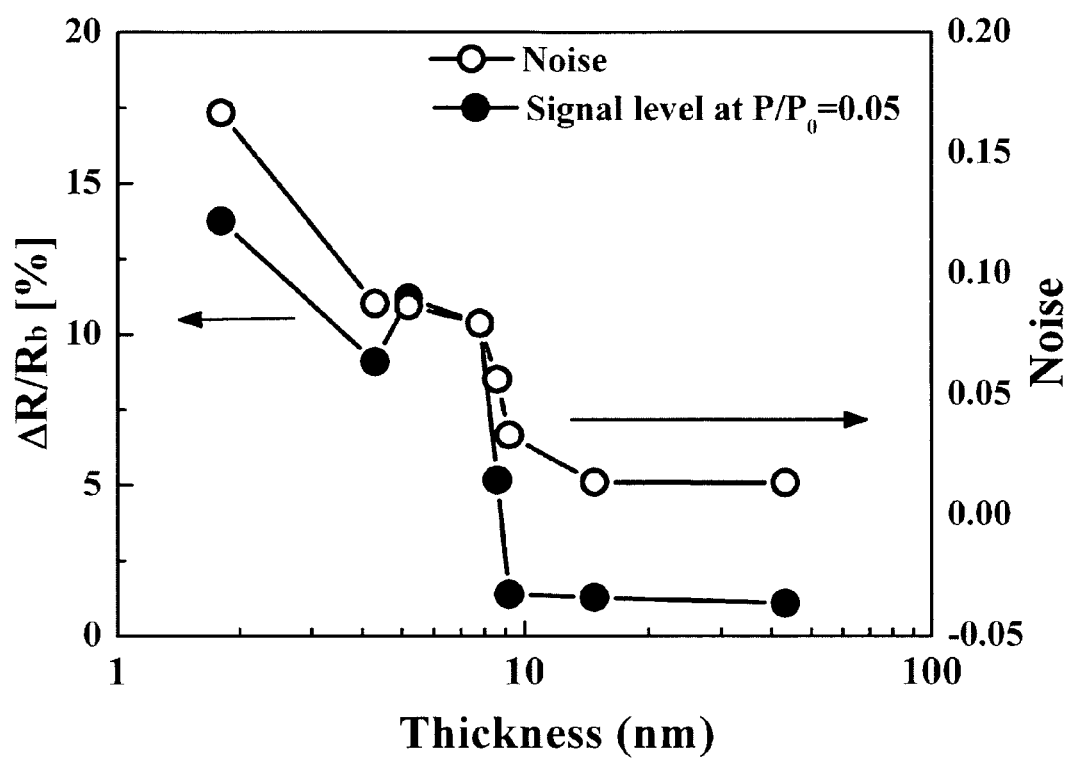
FIG. 4. Relative differential resistance responses $\Delta R/R_b$ (left y-axis), and noise level (right y-axis) at various (average) film thicknesses of gold nanoparticles coated with dodecanethiol ligands upon exposure to decane at 0.05 P/P°.

Example 6: The Effect of Nanoparticle Size Distribution and the Thickness of the Organic Coating on Electronic Response In order to determine the effect of the thickness of the organic coating on the relative differential resistance responses $\Delta R/R_b$, Au nanoparticles having an average diameter of about 5.2 nm which were coated with dodecanethiol ligands at various thicknesses were used. The dodecanethiol-capped Au nanoparticles were exposed to decane at 0.05 P/P° and the $\Delta R/R_b$ values were measured. FIG. 4 shows that the signal levels are highly dependent on the thickness of the organic coating with low responses obtained for thicknesses above 10 nm. The calculated noise shows a similar pattern to that of the signal, indicating that the decrease in signal at thicknesses above 10 nm is not due to an increase in the noise level.

Figure 5:
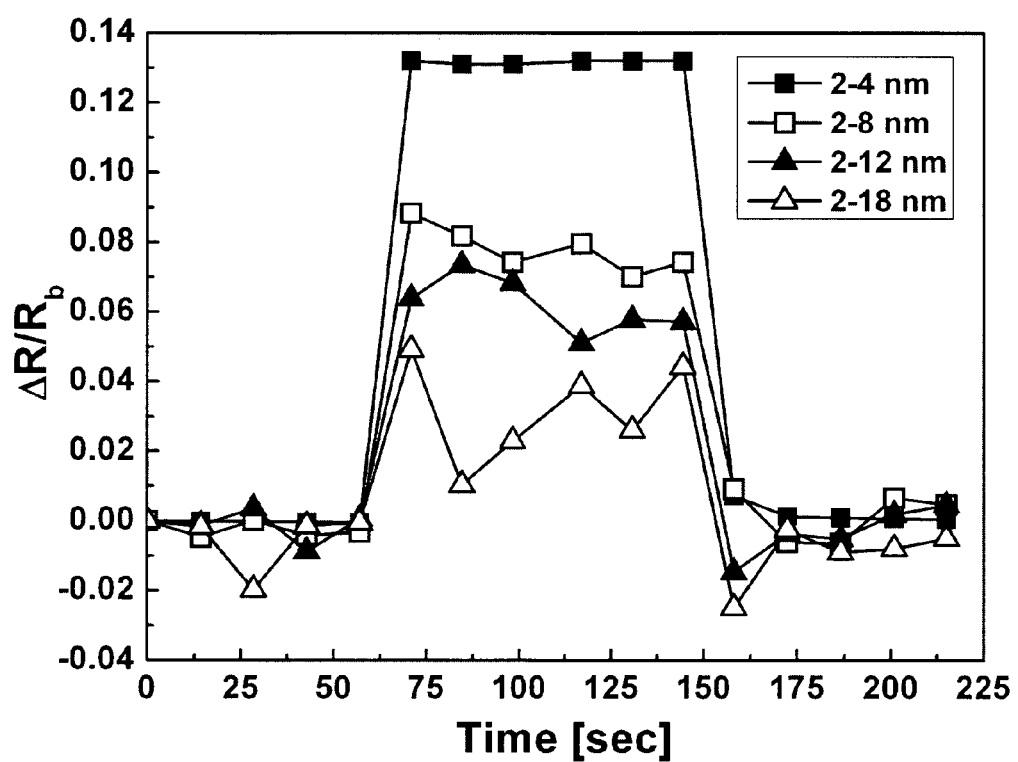
FIG. 5. Response of films of gold nanoparticles coated with hexanethiol ligands having different size distributions to hexane at 0.001 P/P°.

In order to determine the effect of nanoparticles size distribution on the signal of the sensors, hexanethiol-Au nanoparticles having an average core size of about 3.6 nm and sizes which range from about 2 nm to about 18 nm were used. An equal amount of a solution of hexanethiol-Au nanoparticles was applied on separate interdigitated electrodes (where each electrode is separated from its adjacent electrode by 10 m) and exposed to different analytes, such as hexane, heptane, decane, methyl benzene, toluene, ethanol, etc. The sensors were exposed simultaneously to a given analyte at a given concentration. FIG. 5 shows the effect of size distribution on the sensing signal and/or on the signal-to-noise ratios of chemiresistors based on spherical Au nanoparticles capped with hexanethiols. An increase in the size distribution decreases the signal-to-noise ratios and additionally, decreases the response of the sensor.

Thus, utilization of nanoparticles having a narrow size distribution provides enhanced sensing signals with over 10 times the sensing signal obtained from a wider size distribution of nanoparticles (nanoparticle sizes in the range of 2-18 nm). Sensors composed of nanoparticles with narrow size distribution are thus advantageous for detecting VOCs indicative of cancer with very high sensitivities. The thickness of the coating can be further optimized to a particular thickness, according to the organic compounds used, in order to enhance the sensing signals.

Example 7: Response of the Sensor Array to Breath Samples from Healthy Individuals and Patients with Lung Cancer The response of the sensor array to breath samples from healthy individuals and patients with lung cancer was tested. One vacuum source and two switches wherein one side connected to the test chamber, and the other side connected to the vacuum source ("vacuum switch") or breath sample ("sample switch"), were used in these experiments. In a typical experiment, signals of the sensor array elements were collected for 5 minutes of vacuum environment by opening the vacuum switch and closing the sample switch, followed by 5 minutes exposure to breath samples which were collected as described in Example 1 hereinabove, then followed by another 5 minutes of vacuum environment. The last two steps were repeated three times for assessing reproducibility. Data analysis of the signals that were collected from all the sensors in the array, was performed using standard principal component and cluster analysis.

Figure 6A:
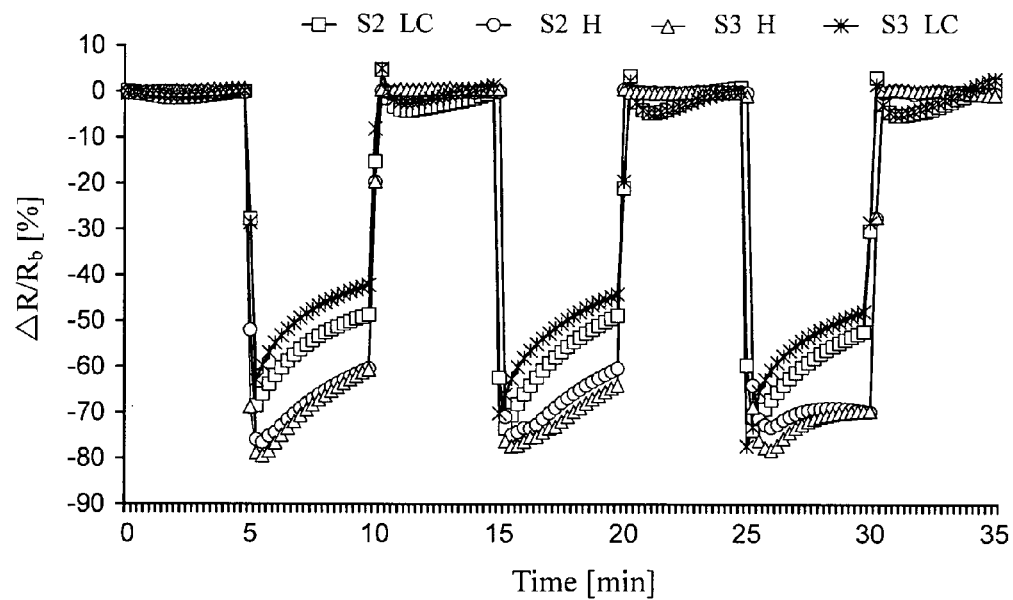
FIG. 6. Relative differential resistance responses, $\Delta R/R_b$ of sensors no. S2 & S3 (6A) and sensors no. S6 & S8 (6B) to breath samples of typical healthy individuals (H) and patients with lung cancer (LC).
Figure 6B:
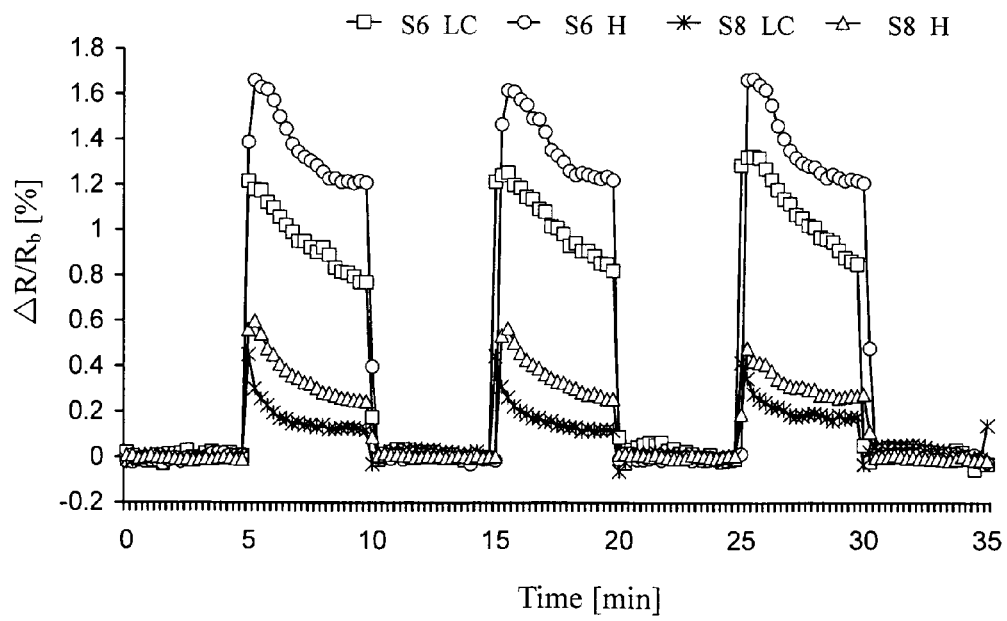

FIGS. 6A and 6B show the relative differential resistance responses, $\Delta R/R_b$ of sensors no. S2, S3 and sensors no. S6, S8, respectively to breath samples that were collected into a bag. The breath samples were obtained from typical lung cancer patients and healthy individuals (controls). The observed responses were rapid (1-10 seconds), completely reversible with extremely good reproducibility for all samples. In particular, sensor no. S2 and sensor no. S3 showed a significant decrease in resistance, while sensor no. S6 and sensor no. S8 showed a small increase in resistance.

In general, two types of responses were seen. The first is a relatively large decrease in chemiresistance as occurred in e.g. S2, S3, S5 and S9. The second is a relatively small increase in chemiresistance as occurred in e.g. S1, S4, S6, S7 and S8. Without being bound by any theory or mechanism of action, the changes in resistance upon analyte exposure could be attributed either to swelling due to an increased interparticle tunnel distance which may increase the resistance or to an increase in the permittivity of the organic matrix surrounding the metal nanoparticles which may decrease the resistance due to a decrease in the activation energy and a reduction of potential well barriers between the metal nanoparticles.

Figure 7A:
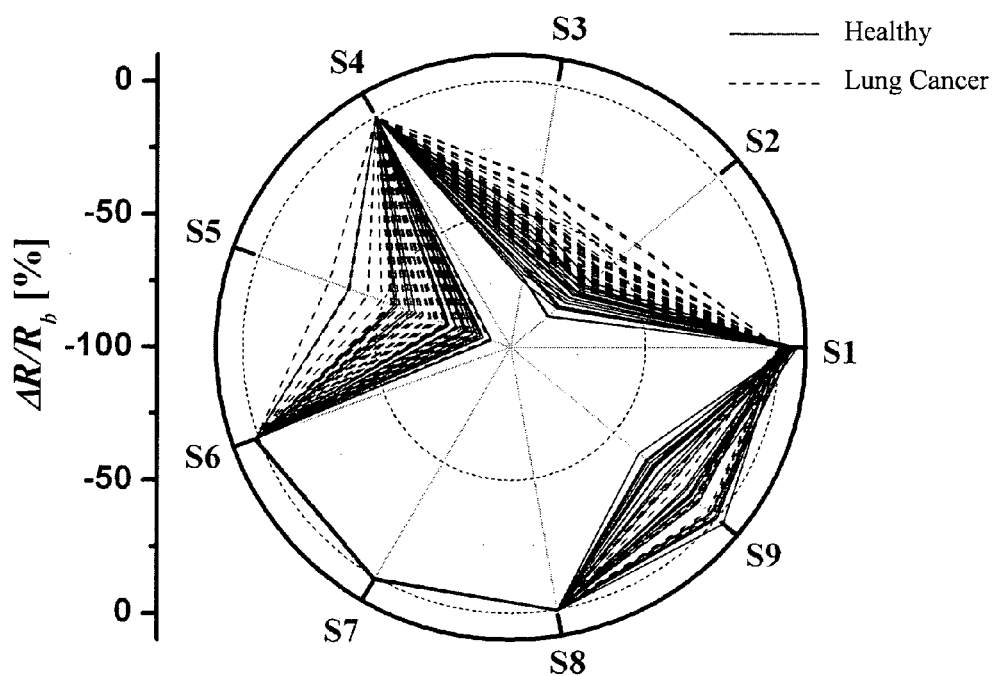
FIG. 7. Response patterns of 90 breath samples of which 64 are breath samples obtained from lung cancer patients (dotted lines) and 26 are breath samples obtained from healthy individuals (continuous lines). (7A) Response patterns using the entire set of sensors. (7B) Response patterns using sensor numbers S1, S4, S6, S7 and S8.
Figure 7B:
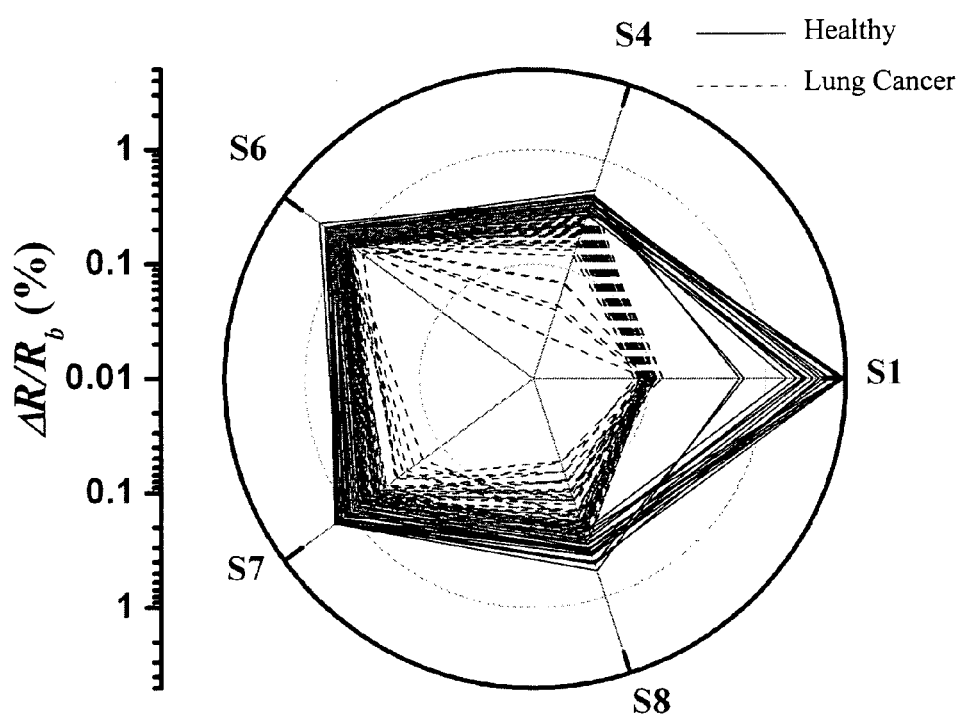
Figure 8:
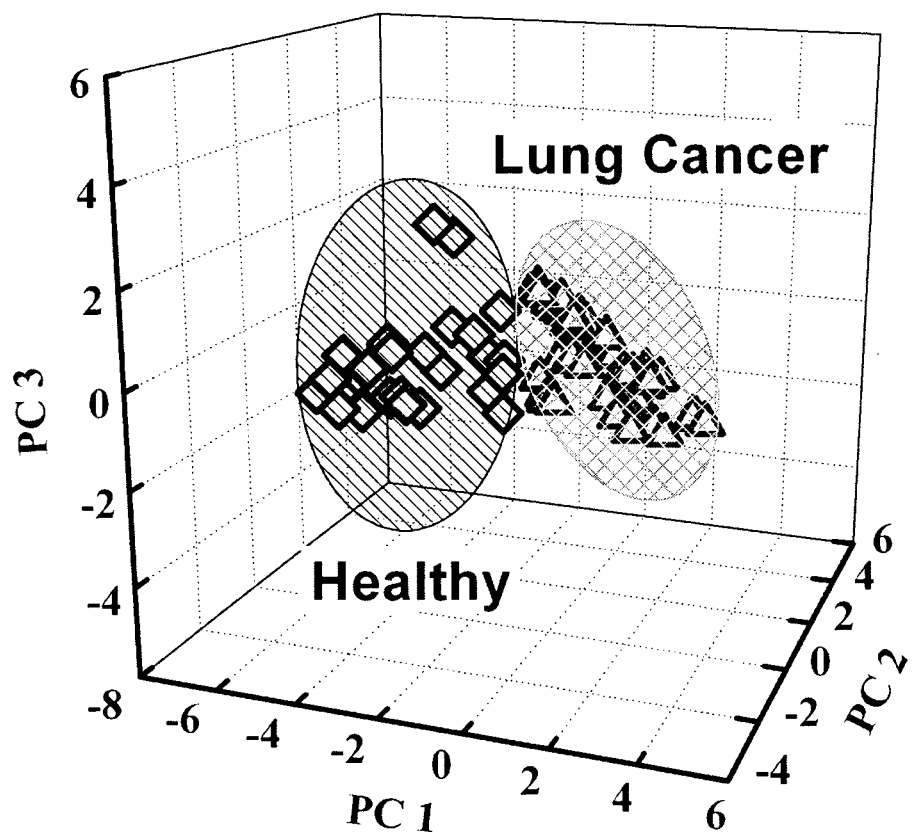
FIG. 8. Data in principal component space from a sensor array having 9 sensors which were exposed to the breath of lung cancer patients (triangles) and the breath of healthy individuals (squares).
Figure 9:
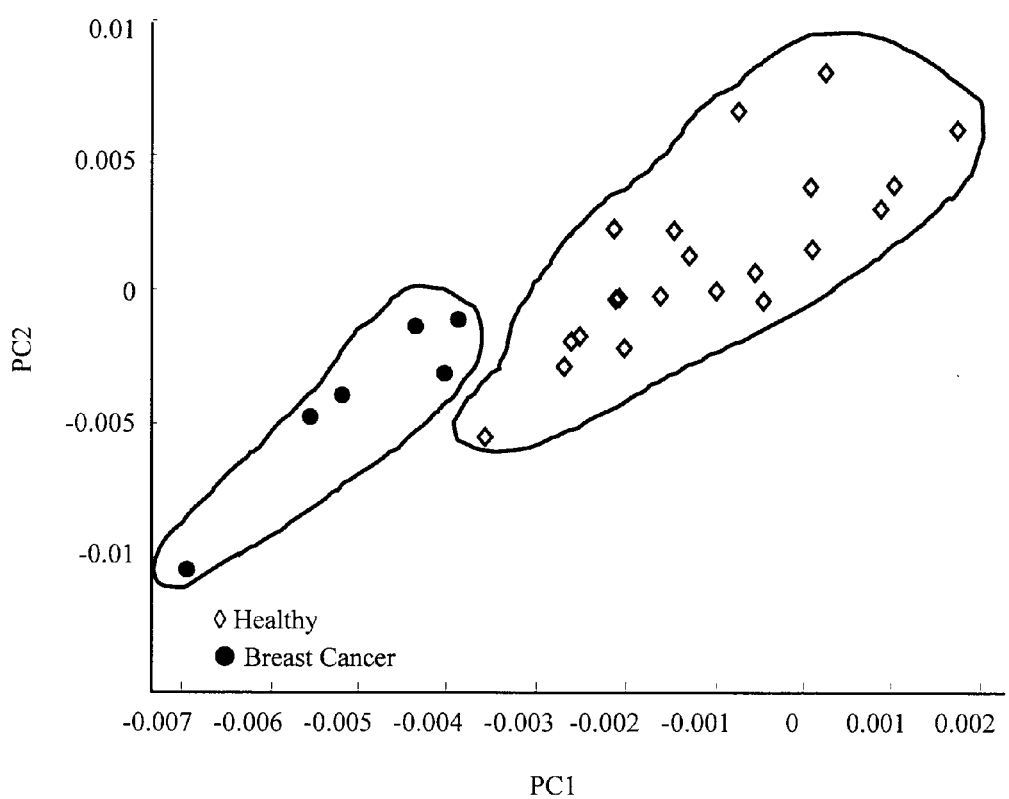
FIG. 9. Data in principal component space from a sensor array having 9 sensors which were exposed to the breath of breast cancer patients (●) and the breath of healthy individuals (◇).
Figure 10:
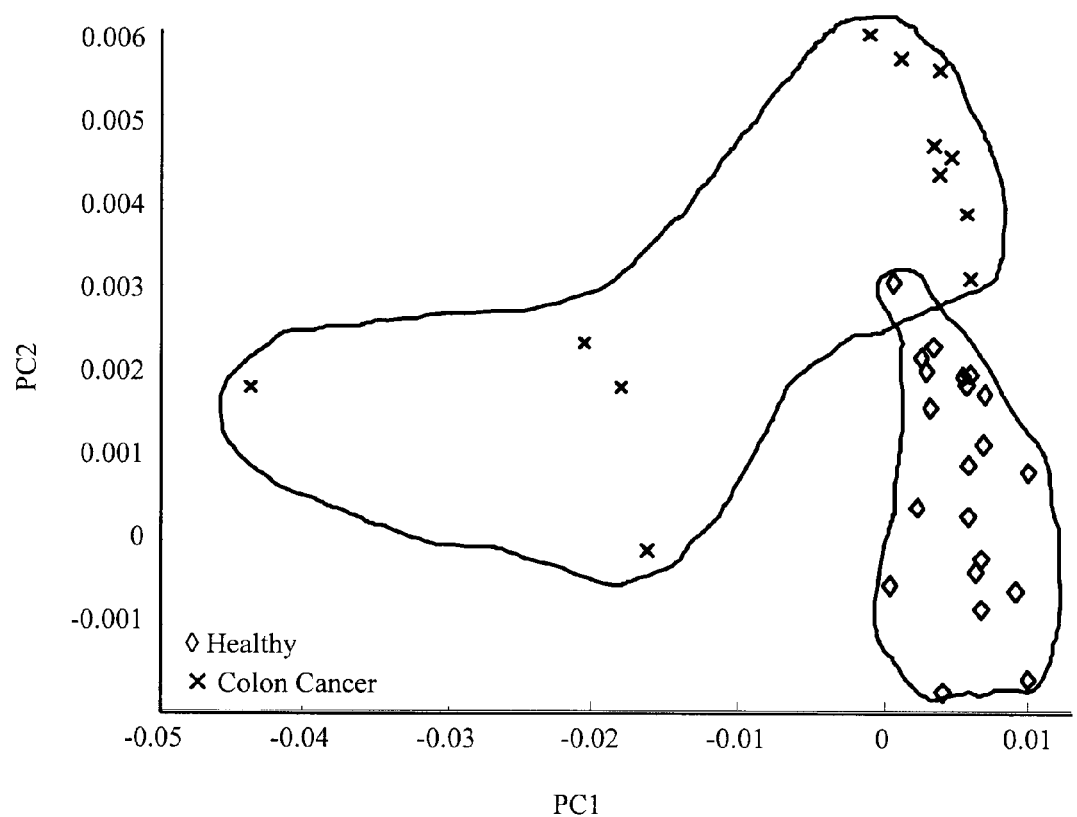
FIG. 10. Data in principal component space from a sensor array having 9 sensors which were exposed to the breath of colon cancer patients (x) and the breath of healthy individuals (◇).
Figure 11:
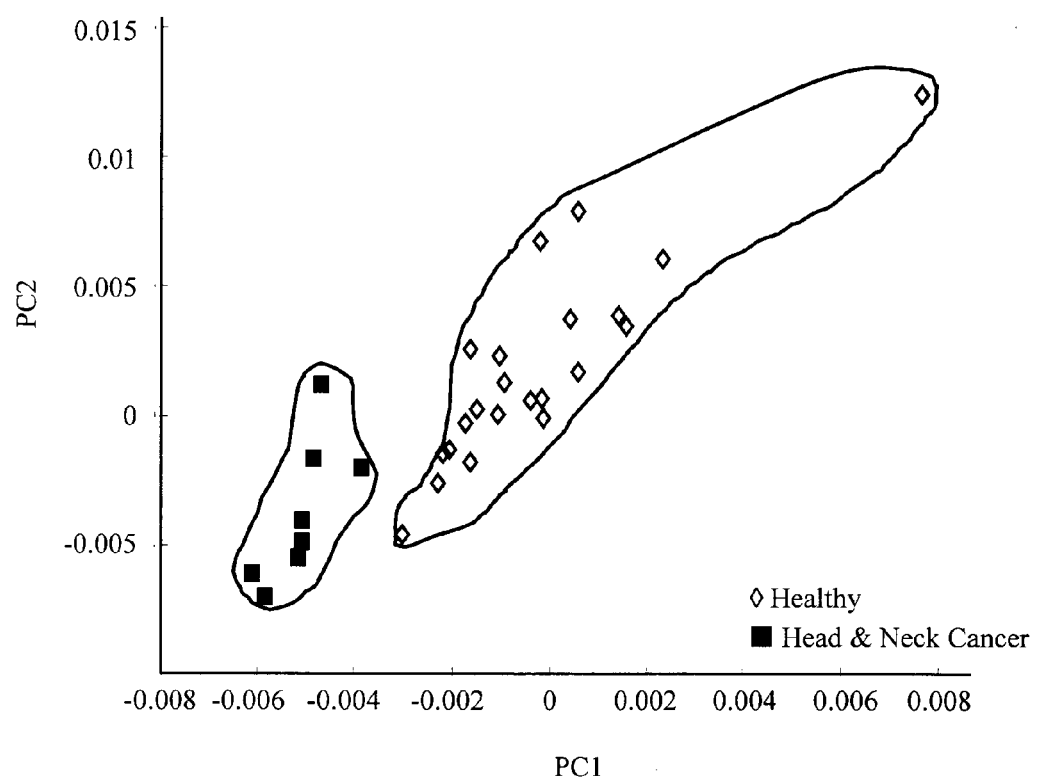
FIG. 11. Data in principal component space from a sensor array having 9 sensors which were exposed to the breath of head and neck cancer patients (■) and the breath of healthy individuals (◇).
Figure 12:
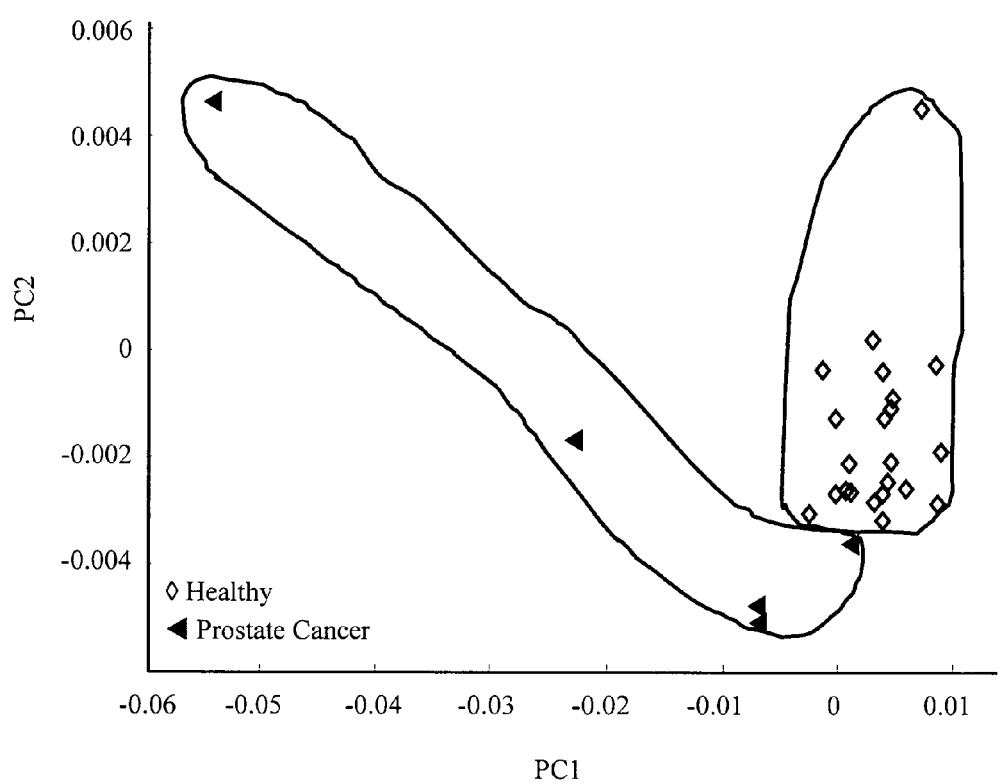
FIG. 12. Data in principal component space from a sensor array having 9 sensors which were exposed to the breath of prostate cancer patients (◄) and the breath of healthy individuals (◊).
Figure 13B:
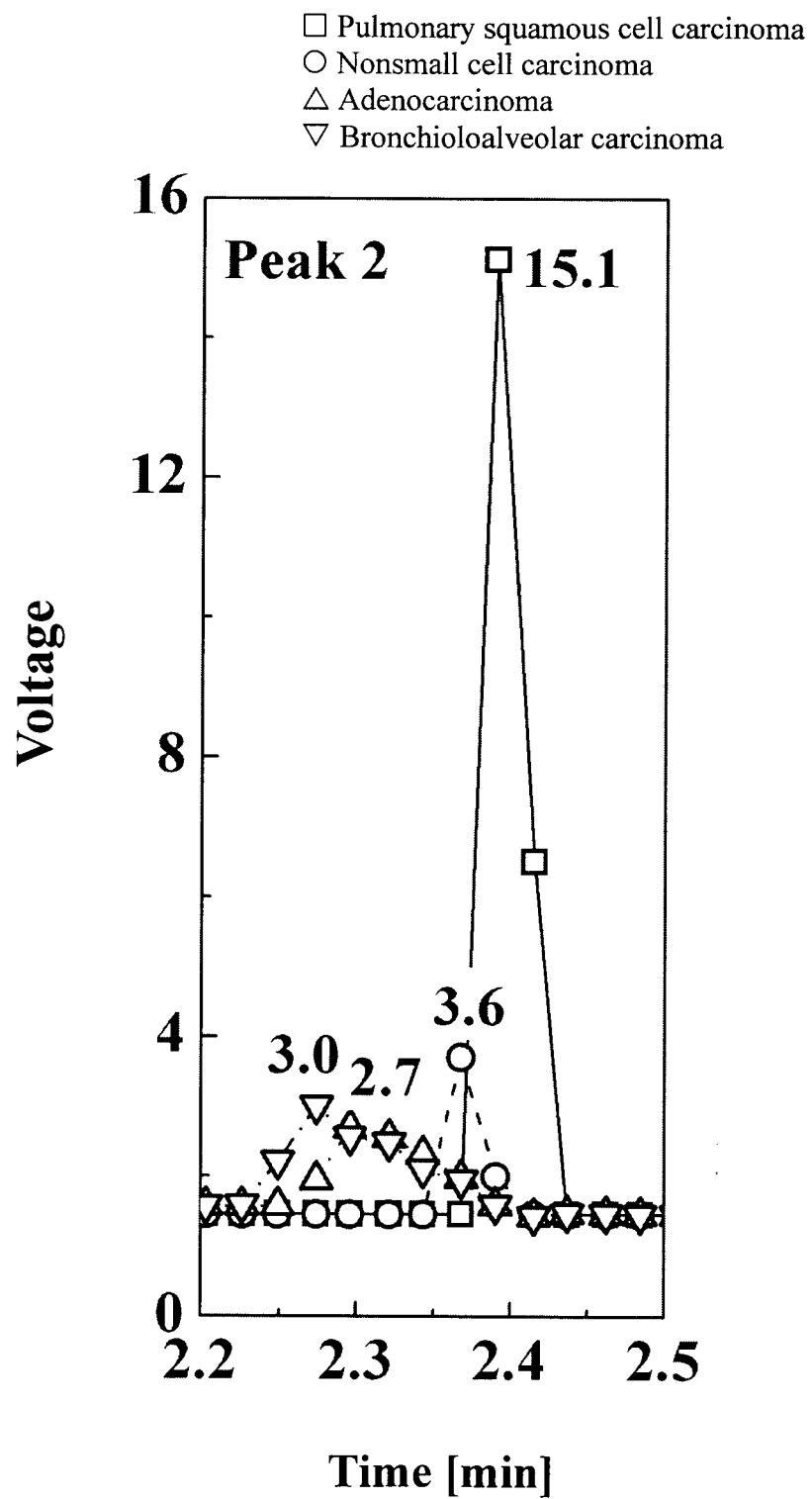
FIG. 13. GC-MS of metabolic VOCs of 4 different lung cancer cells in vitro; (13A) peak 1; (13B) peak 2; (13C) peak 3; and (13D) peak 4. Data is based on GC-MS analysis of pulmonary squamous cell carcinoma (8 patients; □), adenocarcinoma (2 patients; Δ), bronchioloalveolar carcinoma (1 patient; ∇), and nonsmall cell carcinoma (1 patient; ○), as was reported by Chen et al. (*Cancer,* 110(4), 2007, 835).
Figure 13C:
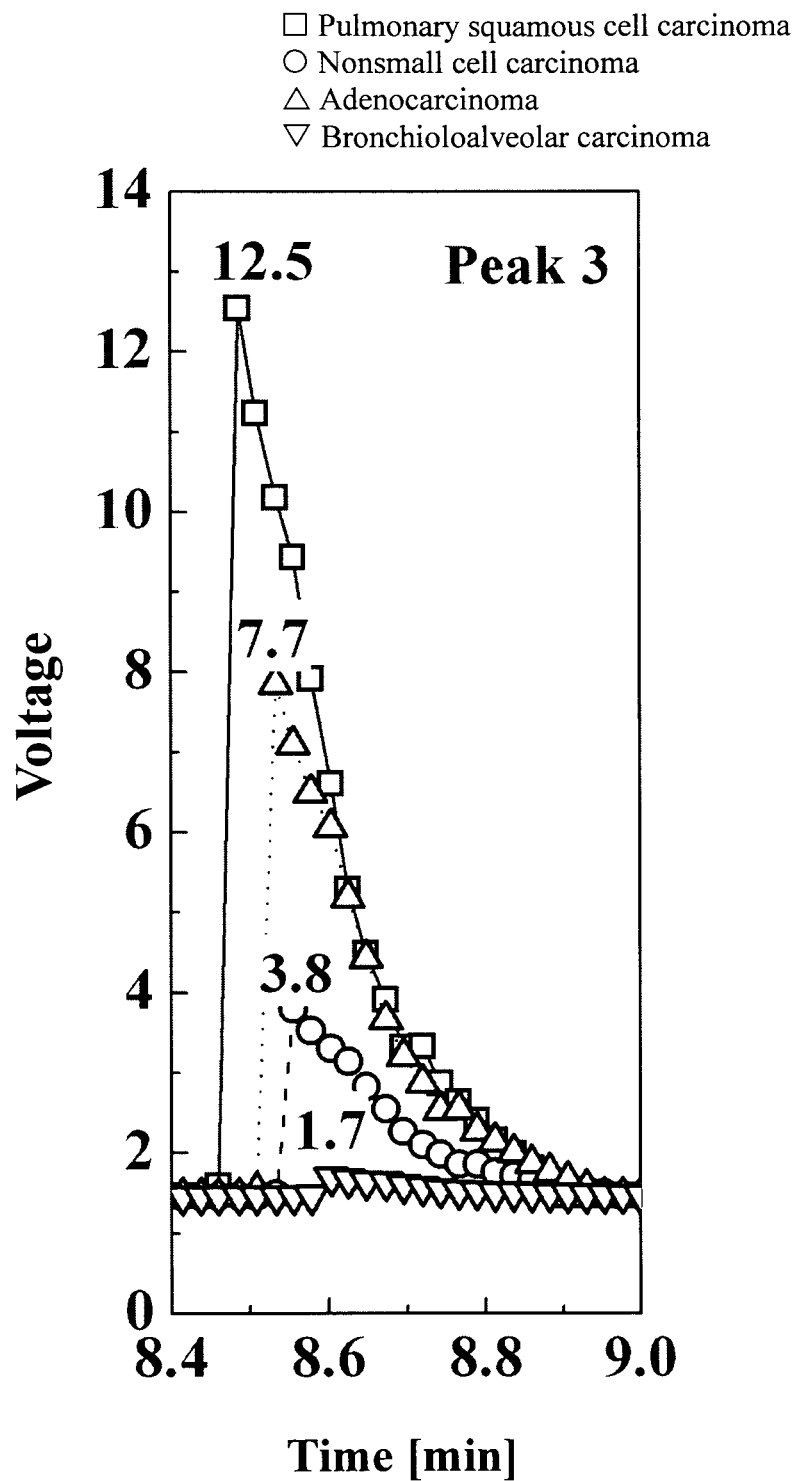
Figure 13D:
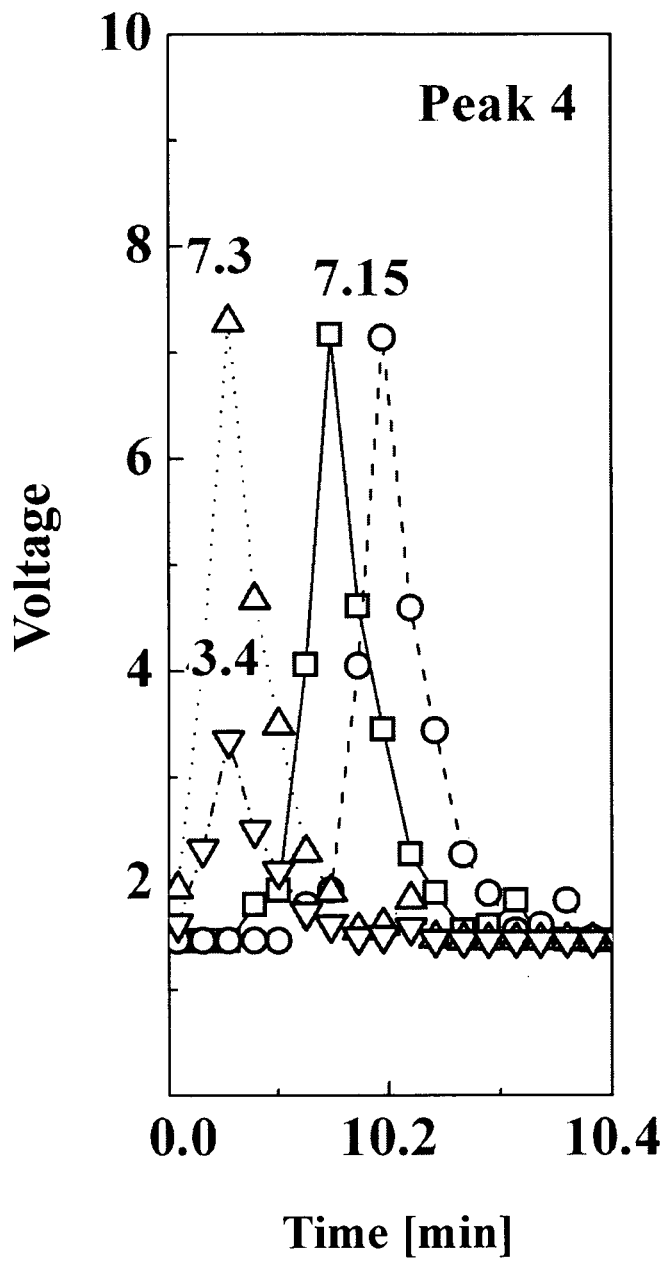

The average response obtained during the first 3 minutes exposure to a given sample in all cycles was calculated. FIGS. 7A-7B shows the patterns in multi-sensor space for all breath samples including 64 breath samples of lung cancer patients and 26 breath samples of healthy individuals. The response to lung cancer breath samples was significantly different than that obtained for healthy individuals breath samples. Although certain sensors provided some overlap between the samples, the pattern of "healthy" samples was unequivocally different from the pattern of "lung cancer" samples. Moreover, principal component analysis (PCA) was used to analyze all the responses from the sensor array. FIG. 8 shows the response in principal component space from a sensor array of 9 sensors (example 4) exposed to breath samples of lung cancer patients and of healthy individuals. It can be seen from FIG. 8 that there is no overlap in the patterns obtained from samples of lung cancer patients and of healthy individuals. Thus, a sensor array of 9 sensors in conjunction with pattern recognition algorithms provides responses with good discrimination between breath patterns of patients having lung cancer and healthy individuals.

Example 8: Response of the Sensor Array to Breath Samples Obtained from Healthy Individuals and Patients with Breast Cancer, Colon Cancer, Head & Neck Cancer, and Prostate Cancer The response of the sensor array to breath samples from healthy individuals and patients with different types of cancer was tested similar to the procedure described in example 7 hereinabove. Particularly, breath samples were obtained from patients suffering from different types of cancers in order to determine the sensor sensitivity to different and distinct patterns of VOCs. The different cancers tested were breast cancer, colon cancer, head & neck cancer, and prostate cancer. FIGS. 9-12 show the response in principal component space of a sensor array of 9 sensors when exposed to breath samples of patients having breast cancer (FIG. 9), colon cancer (FIG. 10), head & neck cancer (FIG. 11), and prostate cancer (FIG. 12) each tested vs. breath samples from healthy individuals.

Using only two principle components, the sensor array of the present invention was able to discriminate between cancer patterns and healthy patterns. Importantly, the discrimination was obtained for various types of cancer. This clearly demonstrates the applicability of the sensor array and system of the present invention for clinical use in diagnosing various types of cancer.

Example 9: Discrimination Between Different Lung Cancer Cells

In order to determine the feasibility of using the sensor array of the present invention for diagnosing lung cancer at different progression stages, samples containing 4 VOCs at different ratios were used. According to Chen et al. (*Cancer*, 110(4), 2007, 835), the ratios of these four VOCs (isoprene, hexane (or hexanal), decane (or trimethyl benzene) and undecane) indicate different stages of the lung cancer disease. For example a mixture of 51.5 ppb of isoprene, 15.1 ppb of hexane (or hexanal), 12.5 ppb of decane (or trimethyl benzene) and 7.2 ppb of undecane can be used to simulated lung cancer breath of pulmonary squamous cell carcinoma. FIGS. 13A-13D show GC-MS results of 4 metabolic VOCs simulating 4 different lung cancer cells, namely, pulmonary squamous cell carcinoma, adenocarcinoma, bronchioloalveolar carcinoma, and nonsmall cell carcinoma in vitro.

Figure 14:
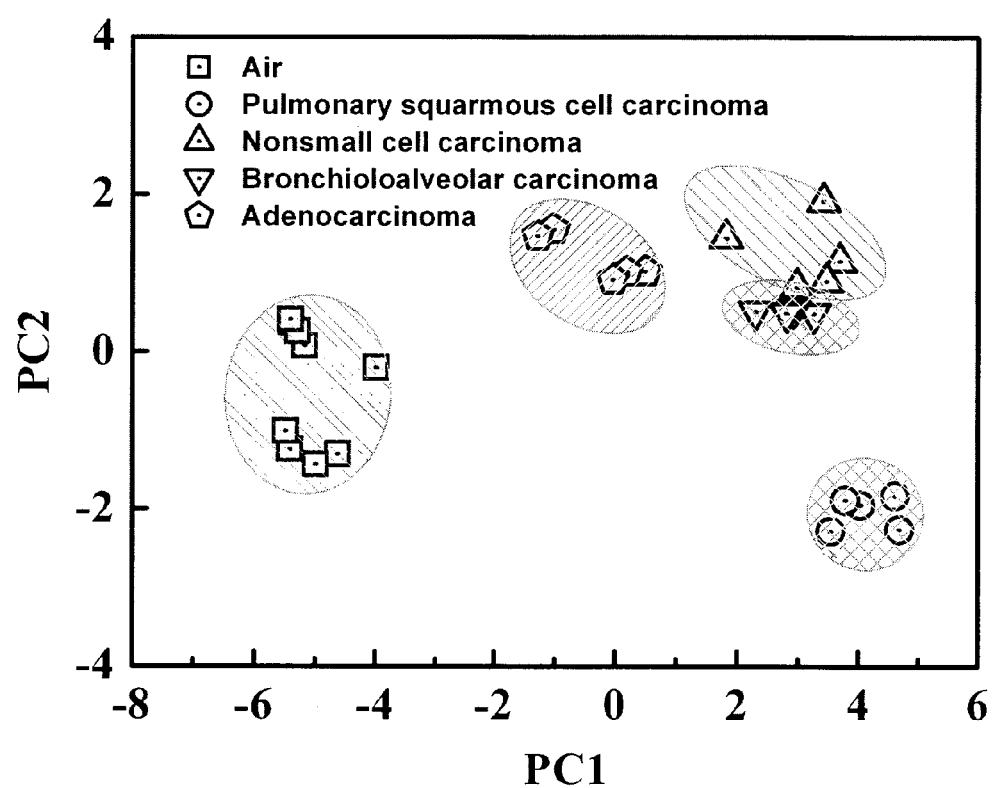
FIG. 14. Data in principal component space from a sensor array having 9 sensors which were exposed to mixtures of VOCs that simulate 4 different lung cancer cells: pulmonary squamous cell carcinoma (circles), adenocarcinoma (pentagons), bronchioloalveolar carcinoma (∇), and nonsmall cell carcinoma (Δ). Isoprene, hexane, decane and undecane were used as the four biomarkers.

Different ratios of the 4 VOCs were then prepared and exposed using a gas generator system to the array of sensors based on Au nanoparticles coated with the organic molecules as described in example 4. Two main simulations were carried out. In the first simulation isoprene, hexane, decane and undecane were used as the four biomarkers. FIG. 14 shows data in principal component space from the sensor array that was exposed to 4 different mixtures of the four biomarkers that simulate lung cancer cells selected from pulmonary squamous cell carcinoma, adenocarcinoma, bronchioloalveolar carcinoma, and nonsmall cell carcinoma. It is evident from these results that the sensor array of 9 sensors is able to discriminate between the different mixtures of VOCs with essentially no overlap between the four conditions.

Figure 15:
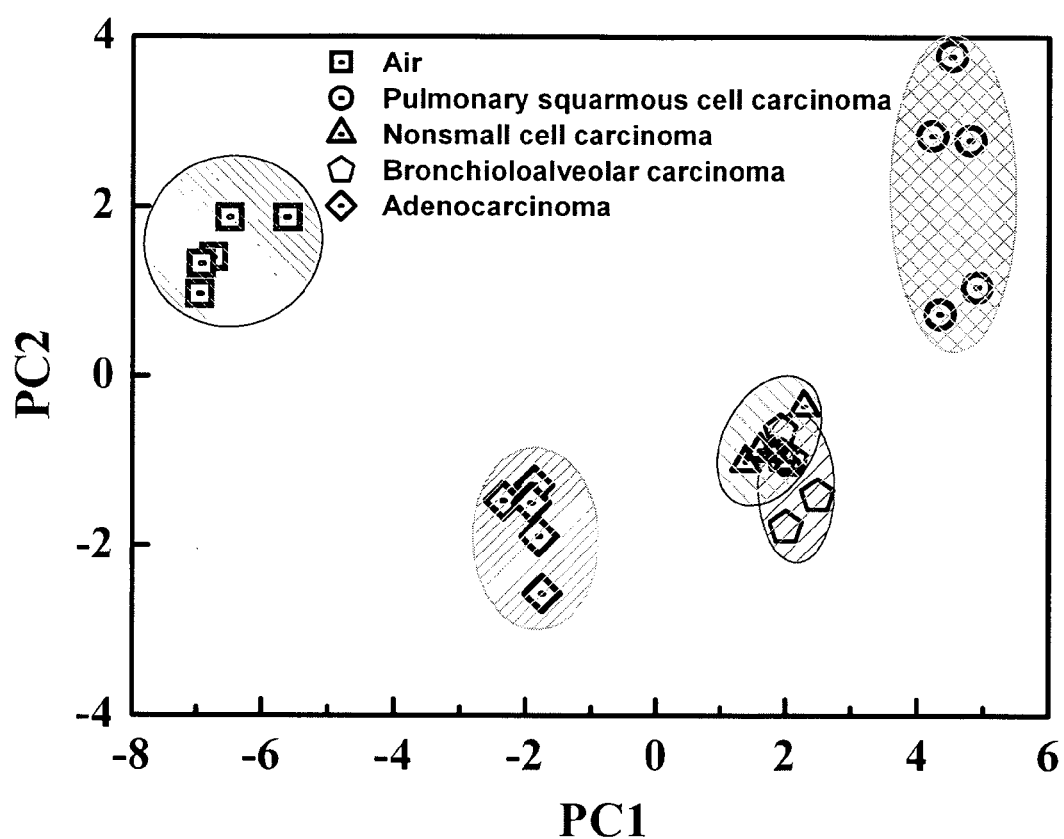
FIG. 15. Data in principal component space from a sensor array having 9 sensors which were exposed to mixtures of VOCs that simulate 4 different lung cancer cells: pulmonary squamous cell carcinoma (circles), adenocarcinoma (◈), bronchioloalveolar carcinoma (pentagons), and nonsmall cell carcinoma (triangles). Isoprene, hexane, trimethyl benzene and undecane were used as the four biomarkers.

In the second simulation isoprene, hexane, trimethyl benzene and undecane were used as the four biomarkers. FIG. 15 shows data in principal component space from the sensor array that was exposed to 4 different mixtures of the four biomarkers that simulate lung cancer cells selected from pulmonary squamous cell carcinoma, adenocarcinoma, bronchioloalveolar carcinoma, and nonsmall cell carcinoma. The sensor array of 9 sensors was capable to discriminate between the different mixtures of VOCs wherein the only overlap is between bronchioloalveolar carcinoma, and nonsmall cell carcinoma. A further separation could be obtained through the use of 3 principle components or through fine tuning of the organic coating.

Hence it is clearly shown, that a sensor array comprising nine sensors of gold nanoparticles capped with alkanethiolates provides high sensitivity to biomarkers indicative of various cancers, and can be used in conjunction with pattern recognition algorithms to provide full discrimination between breath samples of healthy individuals and breath samples of patients suffering from either one of lung cancer, breast cancer, head & neck cancer, colon cancer, and prostate cancer. Additionally, the results presented herein show that the sensor array of the present invention provides discrimination between VOC mixtures simulating different stages (or tumor sizes) of lung cancer. The sensor array of the present invention could thus be used clinically, for early diagnosis of lung cancer as well as other types of cancer.

Example 10: Test Population

Breath samples were taken from 68 volunteers aged 30-75, who had not ingested coffee or alcohol for at least 1 hour and 12 hours, respectively, after signed consent. The volunteers were divided as follows: 22 primary lung cancer patients, 17 primary colon cancer patients, 15 primary breast cancer patients, and 14 primary prostate cancer patients. Additionally, 18 healthy individuals that matched the tested cancer patients in age and lifestyle were used as controls. All cancer patients were tested directly after being diagnosed by conventional clinical methods (e.g. bronchoscope biopsy, computed tomography scan, pulmonary puncture, colonoscopy, mammography etc.) and prior to chemotherapy and/or other cancer treatment. No breath collection was carried out in the 4 days following the biopsy. The clinical characteristics of the study population for cancer patients and healthy volunteers are listed in Table 4. Additional breath samples were taken from 59 healthy volunteers, aged 20-79, for studying the effect of various confounding factors. All experiments were approved by and performed according to the guidelines of the Technion's committee for supervision of human experiments (Haifa, Israel).

TABLE 4

Clinical characteristics of 68 cancer patients and 18 healthy controls. The overall ratio between males and females is ~1:1.

| Cancer Type | Tested by GC-MS | Tested by Sensor array | No. of patients | Smoker (Y/N) | Ex-Smoker (Y/N) | Histology | Stage | Additional data |
|---|---|---|---|---|---|---|---|---|
| Lung Cancer | x | | 1 | Y | | NSCLC[(1)] | 3A | |
| | x | | 1 | Y | | NSCLC | 3A | Diabetes; Takes Glucophage |
| | | x | 1 | Y | | NCSLC | 3A | Ischemic Heart Condition; Takes Plavix, Aspirin. |
| | x | x | 1 | Y | | n/a | 3B | High cholesterol levels, HTIV; Takes Simoville, Aspirin |
| | x | | 1 | N | N | NSCLC | 3B | Diabetes; Takes various medications. |
| | x | x | 1 | N | Y | NSCLC | 3B | Takes Optalgin, Oxycontan |
| | | x | 1 | n/a | n/a | n/a | 3B | |
| | | x | 1 | N | Y | NSCLC | 3 | |
| | x | x | 1 | N | N | NSCLC | 4 | |
| | x | | 1 | N | N | NSCLC | 4 | |
| | x | x | 1 | N | Y | SqCLC[(2)] | 4 | HTIV, Hyperlipidemia; Takes Normiten, Omnic, Simovill |

TABLE 4-continued

Clinical characteristics of 68 cancer patients and 18 healthy controls. The overall ratio between males and females is ~1:1.

| Cancer Type | Tested by GC-MS | Tested by Sensor array | No. of patients | Smoker (Y/N) | Ex-Smoker (Y/N) | Histology | Stage | Additional data |
|---|---|---|---|---|---|---|---|---|
| | x | | 1 | N | N | NSCLC | 4 | Takes Normiten, Simoville, Teraperin, Omperdex |
| | x | | 1 | Y | | NSCLC | 4 | |
| | x | x | 1 | Y | | NSCLC | 4 | |
| | x | | 1 | N | N | NSCLC | 4 | Heart disease; Takes various medications |
| | x | | 1 | Y | | n/a | 4 | High blood pressure; Takes Kaptobril |
| | | x | 1 | n/a | n/a | n/a | 4 | |
| | | x | 1 | N | N | NSCLC | 4 | |
| | | x | 1 | N | N | NSCLC | 4 | Heart attack; Takes Valium |
| | x | | 1 | N | N | NSCLC | n/a | Takes medications, didn't perform the test adequately |
| | x | | 1 | Y | | NSCLC | n/a | |
| | | x | 1 | Y | | NSCLC | n/a | |
| Colon Cancer | | x | 1 | Y | | Tubolovillous adenoma | — | Pre-malignant |
| | x | x | 1 | N | N | Modified AC(3) | 1 | |
| | | x | 1 | N | Y | Rectum AC | 2 | |
| | x | | 1 | Y | | n/a | 2 | |
| | x | | 2 | N | N | n/a | 2 | |
| | x | | 1 | N | N | n/a | 2 | High blood pressure; Takes various medications |
| | x | | 1 | Y | | Rectum AC | 2 | High blood pressure; Takes various medications |
| | x | | 1 | N | N | n/a | 3 | Atrialfibrilation; Takes various medications |
| | x | x | 1 | N | Y | Rectum AC | 3 | Diabetes, high blood pressure; Takes various medications |
| | x | x | 1 | N | Y | Rectum AC | 3 | Hyperlipidemia, high blood pressure; Takes various medications |
| | x | x | 1 | N | N | Rectum AC | 3 | Diabetes, high blood pressure; Takes various medications |
| | x | | 1 | N | N | Rectum AC | 3 | |
| | x | | 1 | N | N | n/a | 4 | |
| | x | | 1 | Y | | Rectum AC | 4 | High blood pressure; Takes Normiten |
| | x | | 1 | Y | | Rectum AC | 4 | |
| | x | x | 1 | Y | | NEC(4) | 4 | |
| Breast Cancer | x | | 1 | N | N | n/a | 1 | Heart disease, High blood pressure, Astrophorosis; Takes various medications |
| | x | | 1 | N | N | n/a | 1 | Thrombocytopenia; Takes various medications |
| | | x | 1 | N | N | IDC(5) | 1 | Gastritis, high blood pressure; Takes various medications |

TABLE 4-continued

Clinical characteristics of 68 cancer patients and 18 healthy controls. The overall ratio between males and females is ~1:1.

| Cancer Type | Tested by GC-MS | Tested by Sensor array | No. of patients | Smoker (Y/N) | Ex-Smoker (Y/N) | Histology | Stage | Additional data |
|---|---|---|---|---|---|---|---|---|
| | x | | 1 | N | N | IDC | 2 | High blood pressure, Hyperlipidemia; Takes Cilaril Plus and Simoville. |
| | | x | 1 | N | N | n/a | 3 | |
| | | x | 1 | N | N | n/a | 3 | Epilepsy; Takes Douplephat, Lamcital and Clonax |
| | x | | 1 | N | N | n/a | n/a | High blood pressure, Diabetes; Takes various medications |
| | x | x | 1 | N | N | IDC | n/a | |
| | x | | 1 | N | N | IDC | n/a | |
| | x | | 1 | N | Y | IDC | n/a | Hypo activity of the thyroid glands; Takes Altroxin and vitamins |
| | | x | 1 | N | N | n/a | n/a | |
| | x | | 1 | N | N | n/a | n/a | |
| | x | | 1 | Y | | n/a | n/a | Several medical conditions; Takes various medications |
| | x | | 1 | N | N | n/a | n/a | Diabetes |
| | x | | 1 | n/a | n/a | n/a | n/a | |
| Prostate Cancer | x | | 1 | N | N | AC | 1 | |
| | x | | 1 | N | N | AC | 1 | Glaukoma; Takes various medications |
| | x | | 1 | N | N | AC | 1 | Diabetes; Takes various medications |
| | | x | 1 | N | N | n/a | 1 | High blood pressure; Takes Enaladex |
| | | x | 1 | N | N | n/a | 1 | Diabetes, Bypass; Takes various medications |
| | x | | 1 | N | N | AC | 1 | High blood pressure; Takes various medications |
| | x | | 1 | N | N | AC | 1 | Diabetes, high blood pressure and Hyperlipidemia; Takes various medications |
| | x | | 1 | N | Y | AC | 1 | Cardiac arrhythmia; Takes various medications |
| | x | | 1 | N | Y | AC | 1 | |
| | x | x | 1 | N | N | AC | 1C | Several health conditions; Takes various medications |
| | x | | 1 | N | N | AC | 2 | Several health conditions; Takes various medications |
| | x | x | 1 | N | N | AC | 2 | Diabetes, Brain stroke two year prior to breath test; Takes various medications |
| | | x | 1 | Y | | n/a | 2 | Back problems; Takes Casodex |
| | | x | 1 | Y | | AC | 4 | High blood pressure; Takes Enaladex and Clexan |
| Healthy Control | x | x | 4 | N | N | | | |
| | x | | 5 | N | N | | | |
| | | x | 2 | N | N | | | |
| | | x | 1 | Y | | | | |

TABLE 4-continued

Clinical characteristics of 68 cancer patients and 18 healthy controls. The overall ratio between males and females is ~1:1.

| Cancer Type | Tested by GC-MS | Tested by Sensor array | No. of patients | Smoker (Y/N) | Ex-Smoker (Y/N) | Histology | Stage | Additional data |
|---|---|---|---|---|---|---|---|---|
| | x | x | 1 | N | N | | | Sub activity of the thyroids glands; Takes Latroxin |
| | x | x | 1 | N | N | | | High blood pressure |
| | x | | 1 | N | N | | | High blood pressure; Takes blood pressure regulating medications |
| | x | | 1 | N | N | | | Takes Altroxyn |
| | x | x | 1 | Y | | | | Diabetes |
| | x | | 1 | n/a | n/a | | | |

[1] NSCLC = Non-Small Cell Lung Carcinoma
[2] SqCLC = Squamous Cell Lung Carcinoma
[3] AC = Adenocarcinoma
[4] Nero-Endocrin Carcinoma
[5] IDC = Invasive Duct Carcinoma Example 11: Breath Collection Exhaled breath was collected in a controlled manner from the test population of example 10. Inhaled air was cleared of ambient contaminants by repeatedly inhaling to total lung capacity for 5 minutes through a mouthpiece (purchased from Eco Medics) that contained a filter cartridge on the aspiratory port, thus removing more than 99.99% of the exogenous VOCs from the air during inspiration. Immediately after lung washout, the subjects exhaled through a separate exhalation port of the mouthpiece against 10-15 cm $H_2O$ pressure to ensure closure of the vellum to exclude nasal entrainment of gas. Exhaled breath contained a mixture of alveolar air and respiratory dead space air. Subjects exhaled into the breath collector which automatically filled the dead space air into a separate bag and the alveolar breath into a 750 ml Mylar sampling bag (polyvinyl fluoride, purchased from Eco Medics) in a single-step process. The Mylar bags were re-used and thoroughly cleaned prior to each use with flowing $N_{2(g)}$ (99.999% purity) for 5-8 minutes (GC-MS in conjugation with pre-concentration techniques showed that this purification process eliminates >99% of the contaminants and/or VOCs from the Mylar bags). At least two bags were collected from each individual for subsequent analysis. All bags were analyzed within two days from the time of breath collection to assure accuracy of the results.

Example 12: Fabrication of the Sensor Array

A sensor array composed of 14 cross-reactive chemiresistors based on assemblies of 5 nm Au nanoparticles coated with different organic compounds was prepared. The nanoparticles were synthesized by a modified two-phase method as described in example 3. The organic compounds that were used for coating the nanoparticles are: dodecanethiol, 4-methoxu-toluenethiol, hexanethiol, 11-mercapto-1-undecanol, decanethiol, octadecanethiol, tert-dodecanethiol, 1-butanethil, 2-ethylhexanethiol, 3-methyl-1-butanethiol, 2-mercaptobenzoxazole, 11-mercapto-1-undecanol, 2-mercaptobenzyl alcohol, and 3-Methyl-1-butanethiol (all purchased from Sigma-Aldrich).

Ten pairs of circular interdigitated gold electrodes were deposited by an e-beam evaporator TFDS-870 (Vacuum Systems & Technologies Ltd., Israel) on device quality silicon wafers capped with 300 nm thermal oxide (purchased from Silicon Quest International Inc., Santa Clara, Calif.). The outer diameter of the circular electrode area was 3000 μm; the gap between two adjacent electrodes and the width of each electrode were both 20 μm. The coated Au nanoparticles were dispersed in chloroform by sonication and drop casted onto the electrodes. While still coated with solution, the substrate was blown with dry $N_2$. This process was repeated several times to yield a desired resistance of about 1 MΩ. The device was dried for 2 hours at an ambient temperature and then placed in a vacuum oven at 50° C. in overnight. The sensors were then mounted onto a custom PTFE circuit board to form the sensor array of 14 sensors.

Example 13: Breath Testing

Figure 16A:
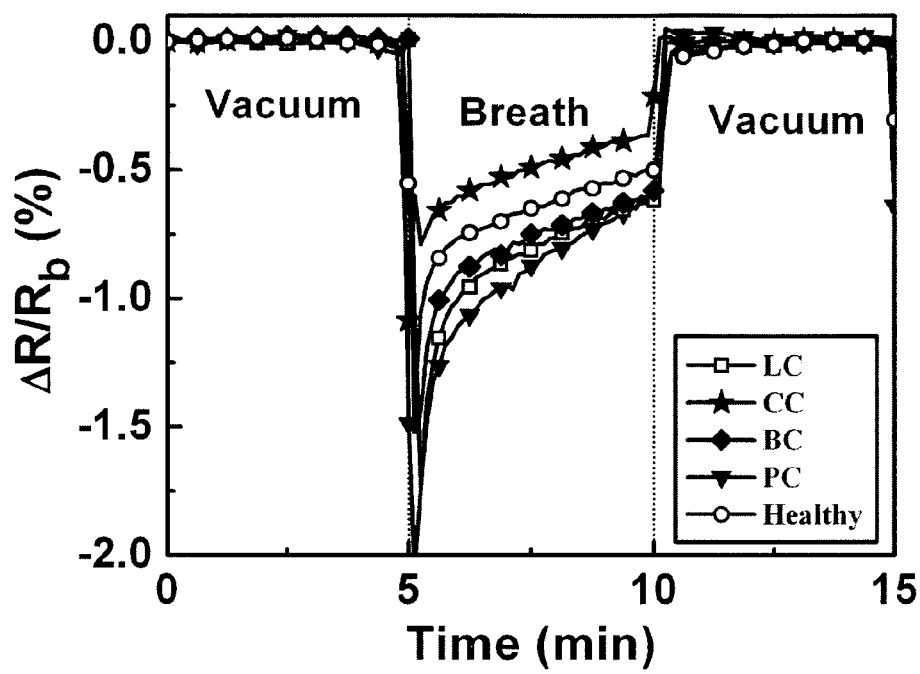
FIG. 16. Clinical characteristics of 68 cancer patients (22 lung cancer, LC squares; 17 colon cancer, CC stars; 15 breast cancer, BC diamonds; and 14 prostate cancer, PC triangles) and 18 healthy controls (circles). No inclusion/exclusion criteria were applied in this group of volunteers. The sensor array was not influenced by confounding factors (such as gender, age or smoking habits). The Au nanoparticles were coated with (16A) 2-ethylhexanethiol, (16B) decanethiol, and (16C) 2-mercaptobenzoxazole.
Figure 16B:
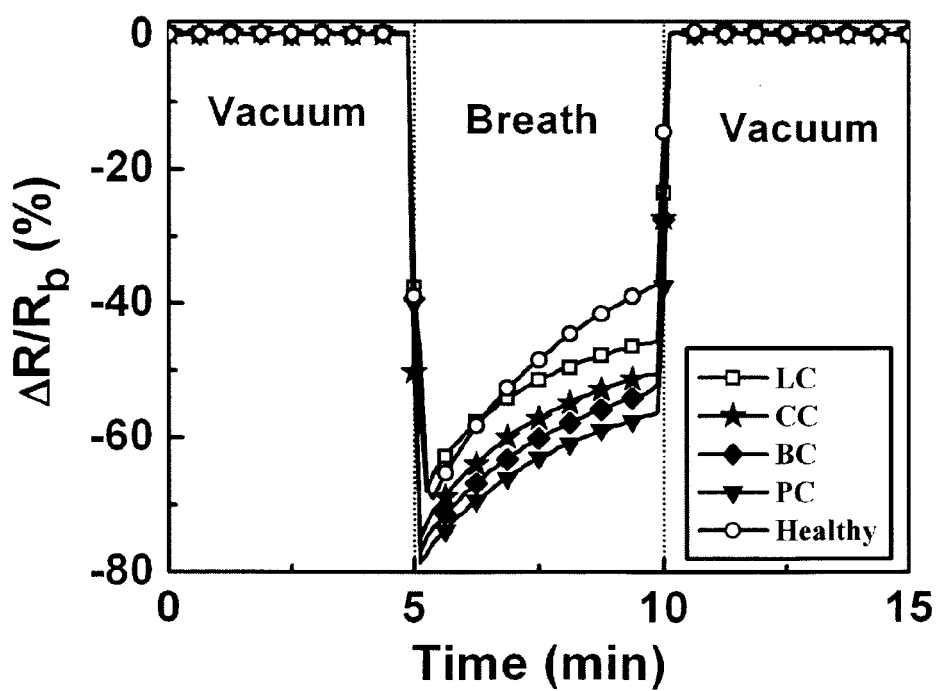
Figure 16C:
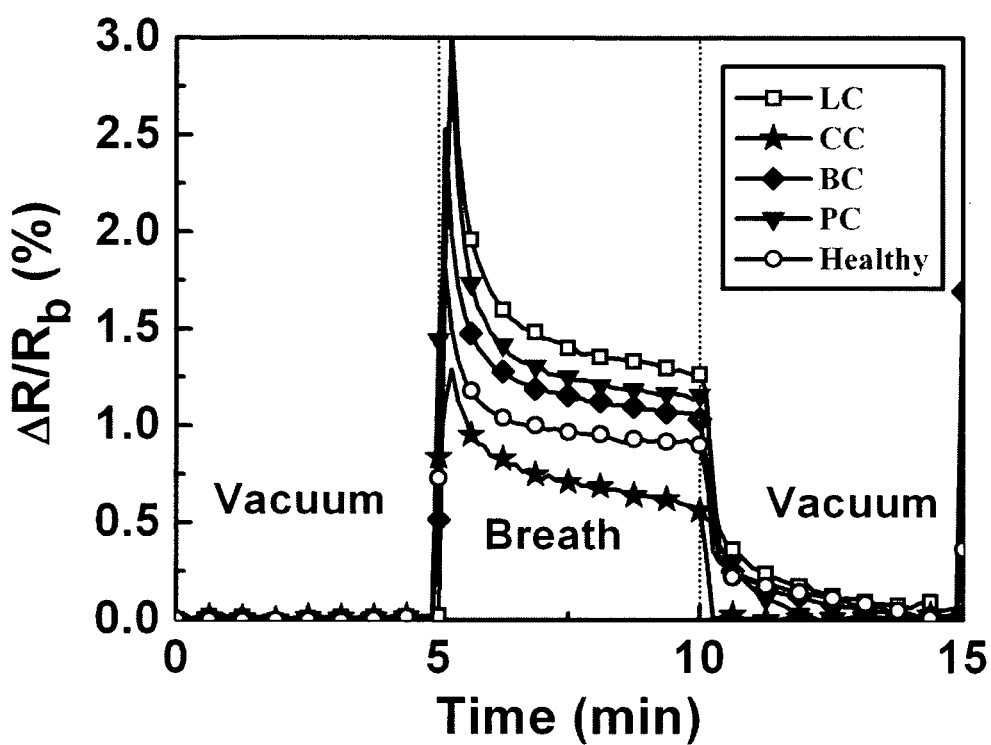

Prior to the exposure of the sensor array of example 12 to breath samples, the responses of each sensor to the breath of lung cancer, colon cancer, breast cancer and prostate cancer patients as well as to the breath of healthy controls were examined (FIGS. 16A, 16B and 16C). The sensors of the present invention responded rapidly to the breath samples of all cancer patients. The responses were fully reversible. Most of the sensors showed detection limit of 1-5 ppb. Additionally, Au nanoparticles that were coated with 4-methoxy-toluenethiol, 2-mercaptobenzoxazole, or 11-mercapto-1-undecanol showed detection limits of 2-10 ppb upon exposure to acetaldehyde (a promising VOC for lung cancer; Smith et al., Rapid Commun. Mass Spectrom., 17, 2003, 845) and formaldehyde (a promising VOC for breast cancer; Ebeler et al., J. Chromatog. B, 702, 1997, 211), much below the concentration level of these VOCs in exhaled breath of cancer patients (Peng et al., Nature Nanotechnol., 4, 2009, 669).

Figure 17A:
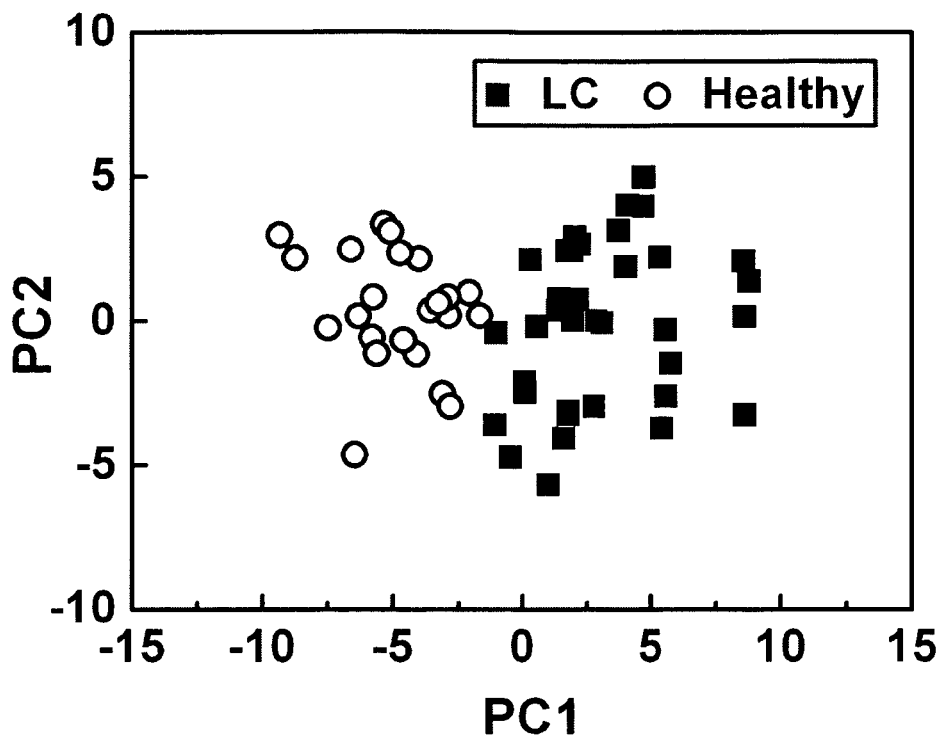
FIG. 17. PCA plots of the sensor array resistance responses to (17A) lung cancer (LC) and healthy controls, (17B) colon cancer (CC) and healthy controls, (17C) breast cancer (BC) and healthy controls, (17D) prostate cancer (PC) and healthy controls and (17E) all cancer patients and healthy controls breath samples.
Figure 17B:
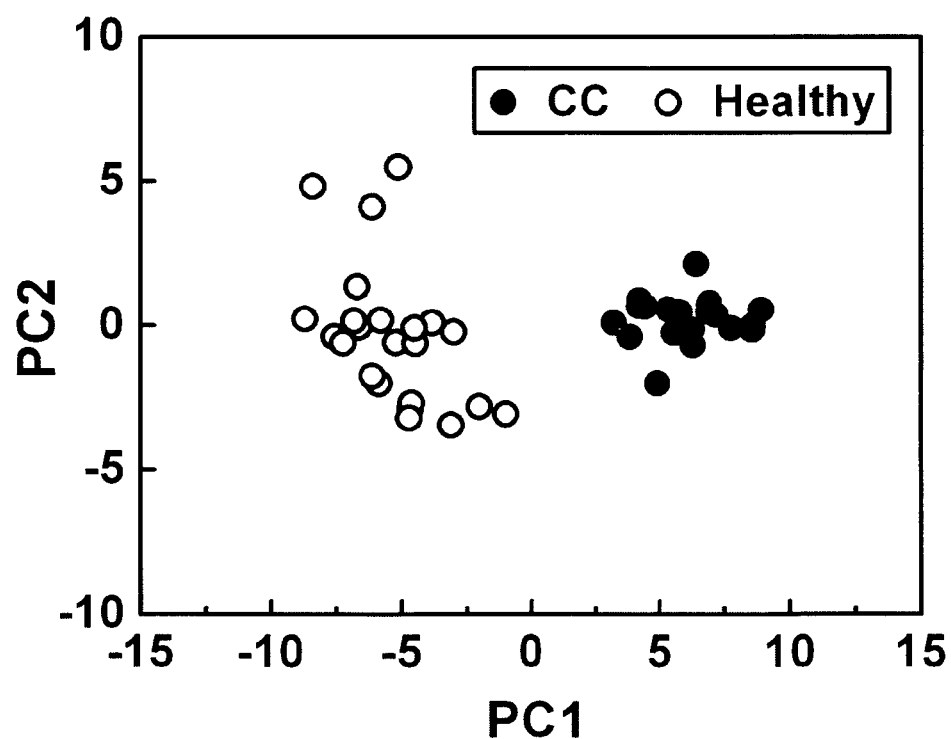
Figure 17C:
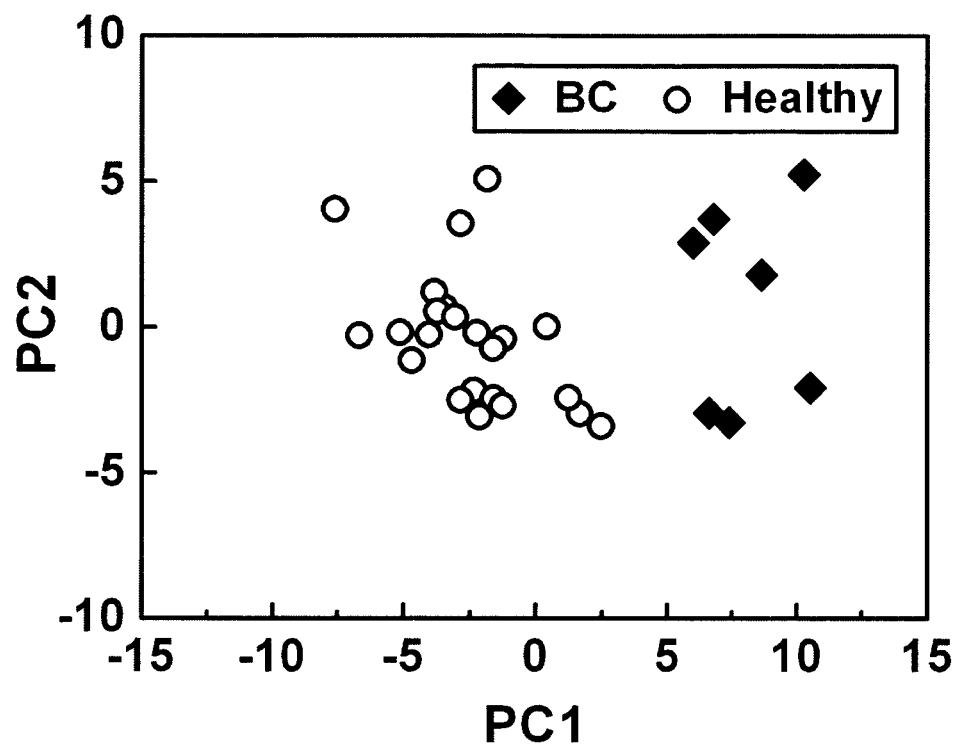
Figure 17D:
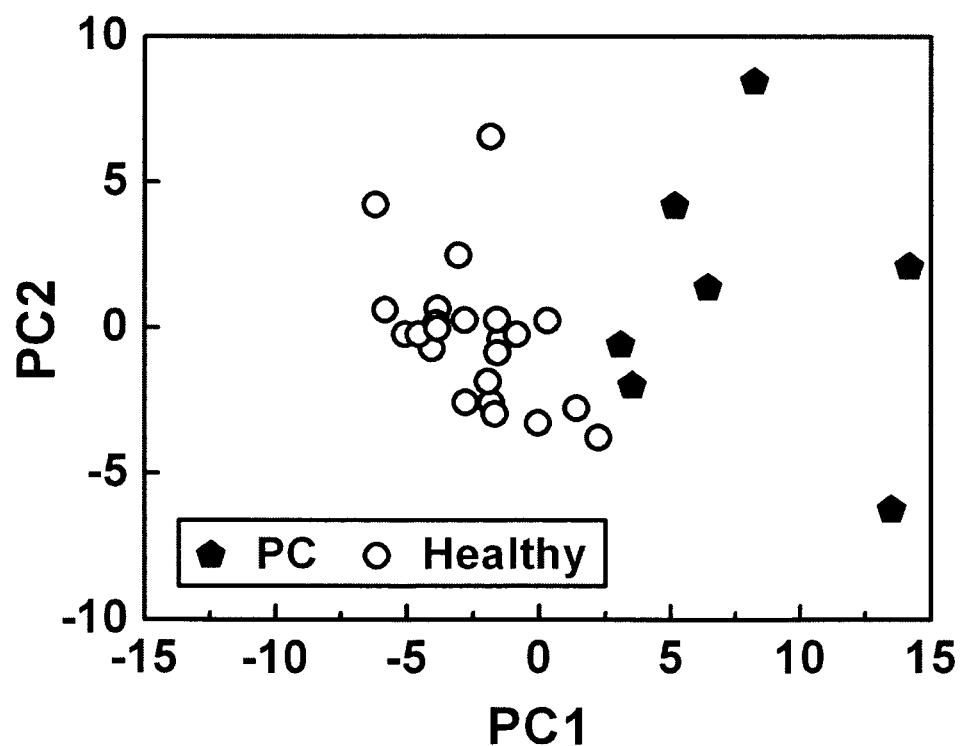
Figure 17E:
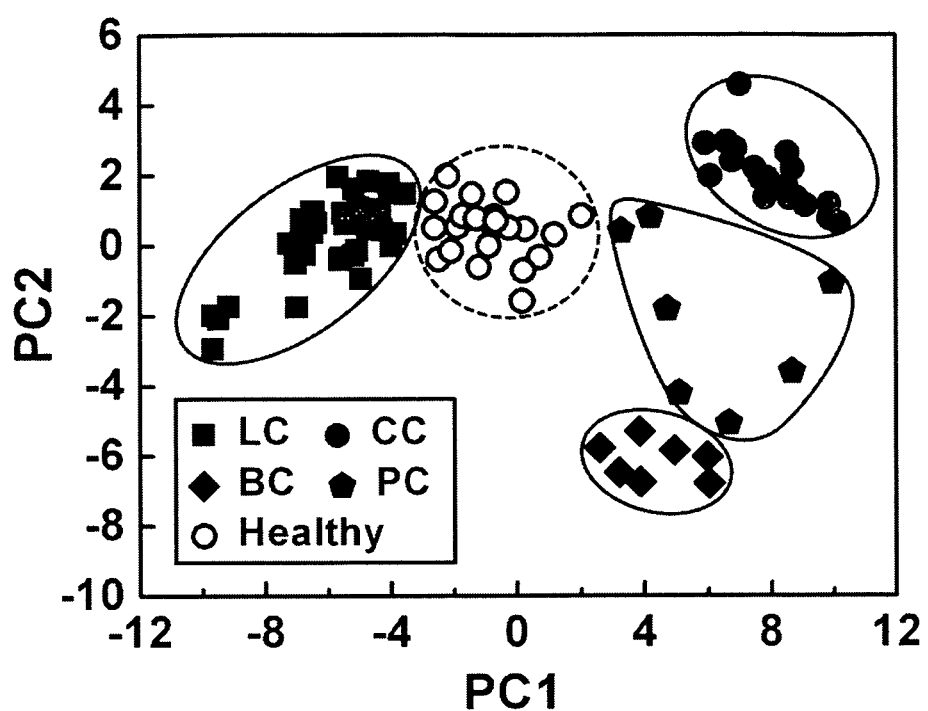

The response of the 14-sensor array to healthy, lung cancer, colon cancer, prostate cancer and breast cancer breath samples was analyzed using principal component analysis (PCA). FIGS. 17A-17E show the first two principal components (PC1 and PC2) for each subject, which accounted for >88% variance. A very good separation between healthy and cancer patterns was obtained, for each cancer type separately (FIGS. 17A-17D) and also for all cancer types in a single plot (FIG. 17E). Of note is that these results were achieved without any pre-treatment (pre-concentration or de-humidification) of the breath samples. Hence, a sensor array comprising 14 sensors of gold nanoparticles capped with an organic coating provides high sensitivity to biomarkers indicative of various types of cancer. The sensor array in conjunction with pattern recognition algorithms provides full discrimination between breath samples of healthy controls and breath samples of patients suffering from either one of lung cancer, breast cancer, colon cancer, and prostate cancer.

It is appreciated by persons skilled in the art that the present invention is not limited by what has been particularly shown and described hereinabove. Rather the scope of the present invention includes both combinations and subcombinations of various features described hereinabove as well as variations and modifications. Therefore, the invention is not to be constructed as restricted to the particularly described embodiments, and the scope and concept of the invention will be more readily understood by references to the claims, which follow.

The invention claimed is:

1. A sensor array comprising conductive nanoparticles capped with an organic coating in a configuration selected from 1D wires, 2D films, and 3D assemblies, wherein the conductive nanoparticles have a narrow particle size distribution with a mean particle size of 3.5-5 nm, particle sizes in the range of 1-10 nm and a width of the distribution curve at one half of the maximum (FWHM) value being less than or equal to 60% of the mean particle size, and wherein the thickness of the organic coating is in the range of 0.2-4 nm, the sensor array being sensitive to volatile organic compounds at concentrations of less than 1 ppm, wherein the conductive nanoparticles capped with an organic coating are not interlinked through linker molecules.

2. The sensor array according to claim 1, wherein the conductive nanoparticles capped with the organic coating are self-assembled and the particle sizes are either in the range of 2-8 nm or in the range of 3-6 nm.

3. The sensor array according to claim 1, wherein the thickness of the organic coating is in the range of 0.6-2 nm.

4. The sensor array according to claim 1, wherein the organic coating comprises a monolayer or multilayers of organic compounds selected from small molecules, monomers, oligomers and polymers, or wherein the organic coating is selected from the group consisting of alkylthiols with $C_3$-$C_{24}$ chains, ω-functionalized alkanethiolates, arenethiolate, (γ-mercaptopropyl)trimethyloxysilane, dialkyl disulfides, xanthates, oligonucleotides, polynucleotides, peptides, proteins, enzymes, polysaccharides, phospholipids, and combinations thereof.

5. The sensor array according to claim 1, wherein the conductive nanoparticles are selected from the group consisting of Au, Ag, Ni, Co, Pt, Pd, Cu, Al, Au/Ag, Au/Cu, Au/Ag/Cu, Au/Pt, Au/Pd, Au/Ag/Cu/Pd, Pt/Rh, Ni/Co, and Pt/Ni/Fe.

6. The sensor array according to claim 1, further comprising at least one component selected from the group consisting of a chemiresistor, chemicapacitor, quartz crystal microbalance, bulk acoustic wave (BAW) and surface acoustic wave (SAW) resonator, electrochemical cell, surface plasmon resonance (SPR), and optical spectroscope.

7. The sensor array according to claim 1, wherein exposure of the array to volatile organic compounds results in a measurable change in one or more of conductivity, resistance, impedance, capacitance, inductance, or optical properties of the array.

8. The sensor array according to claim 7, wherein the measurable change in one or more of conductivity, resistance, impedance, capacitance, inductance, or optical properties of the array is provided by the aggregation or swelling of the conductive nanoparticles capped with an organic coating assemblies upon adsorption of the volatile organic compounds on the capped nanoparticles.

9. The sensor array according to claim 1, wherein the array is essentially insensitive to water vapor at concentrations of 0.001-0.05 P/P°.

10. A system comprising: the sensor array according to claim 1, and a learning and pattern recognition analyzer, wherein the learning and pattern recognition analyzer receives sensor output signals and compares them to stored data.

11. The system according to claim 10, wherein the conductive nanoparticles have particle size in the range of 2-8 nm or wherein the conductive nanoparticles have particle size in the range of 3-6 nm.

12. The system according to claim 10, wherein the thickness of the organic coating is in the range of 0.6-2 nm.

13. The system according to claim 10, wherein the organic coating comprises a monolayer or multilayers of organic compounds selected from small molecules, monomers, oligomers and polymers, or wherein the organic coating is selected from the group consisting of alkylthiols with $C_3$-$C_{24}$ chains, ω-functionalized alkanethiolates, arenethiolate, (γ-mercaptopropyl)trimethyloxysilane, dialkyl disulfides, xanthates, oligonucleotides, polynucleotides, peptides, proteins, enzymes, polysaccharides, phospholipids, and combinations thereof.

14. The system according to claim 10, wherein the conductive nanoparticles are selected from the group consisting of Au, Ag, Ni, Co, Pt, Pd, Cu, Al, Au/Ag, Au/Cu, Au/Ag/Cu, Au/Pt, Au/Pd, Au/Ag/Cu/Pd, Pt/Rh, Ni/Co, and Pt/Ni/Fe.

15. The system according to claim 10, further comprising at least one component selected from the group consisting of a chemiresistor, chemicapacitor, quartz crystal microbalance, bulk acoustic wave (BAW) and surface acoustic wave (SAW) resonator, electrochemical cell, surface plasmon resonance (SPR), and optical spectroscope.

16. The system according to claim 10, wherein the learning and pattern recognition analyzer comprises at least one algorithm selected from the group consisting of artificial neural network algorithms, principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

17. The system according to claim 10, further comprising an apparatus for collecting breath samples, wherein the apparatus is designed to collect alveolar breath.

18. The system according to claim 17, further comprising at least one of a breath concentrator and a dehumidifying unit.

19. A method of diagnosing cancer in a subject, the method comprising the steps of:
(i) providing a system comprising a the sensor array according to claim 1, and a learning and pattern recognition analyzer, wherein the learning and pattern recognition analyzer receives sensor signal outputs and compares them to stored data;

(ii) exposing the sensor array to an exhaled breath sample from the subject; and (iii) using a learning and pattern recognition algorithm to determine the presence of a pattern of volatile organic compounds indicative of cancer in the sample.

20. The method according to claim 19, further comprising differentiating between different types of cancer or between different stages of a single cancer type.

21. The method according to claim 19, wherein the cancer is selected from the group consisting of lung, head and neck, breast, prostate, colon, ovarian, kidney, bladder, oral, and skin cancers.

22. The method according to claim 19, wherein the volatile organic compounds indicative of cancer are selected from the group consisting of 4-methyl-octane, 2-ethyl-1-hexanol, 2-ethyl-4-methyl-1-pentanol, 2,3,4-trimethyl-pentane, 2,3-dimethyl-hexane, trimethylsilyl fluoride, dimethyl-silanediol, 3-ethyl-3-methyl-2-pentanone, 2-methyl-4,6-octadiyn-3-one, 2-propyl-1-pentanol, decane, trimethyl benzene, ethyl benzene, heptanol, isoprene, hexane, undecane and 6,10-dimethyl-5,9-dodecadien-2-one.

* * * * *

UNITED STATES PATENT AND TRADEMARK OFFICE
CERTIFICATE OF CORRECTION

PATENT NO. : 9,696,311 B2
APPLICATION NO. : 13/143227
DATED : July 4, 2017
INVENTOR(S) : Haick et al.

Page 1 of 1

It is certified that error appears in the above-identified patent and that said Letters Patent is hereby corrected as shown below:

On the Title Page

Page 2, Column 2 Line 5, Joseph, Yvonne et al. reference, delete "nanoparticlelorganic" and insert -- nanoparticle/organic --.

In the Claims

Column 34:
Line 66 (Claim 19, Line 3), after "(i) providing", delete "a system comprising a".

Signed and Sealed this
Twelfth Day of September, 2017

Joseph Matal
*Performing the Functions and Duties of the
Under Secretary of Commerce for Intellectual Property and
Director of the United States Patent and Trademark Office*